(12) United States Patent
Yoon et al.

(10) Patent No.: US 10,890,557 B2
(45) Date of Patent: Jan. 12, 2021

(54) ELECTROCHEMICAL BIOSENSOR

(71) Applicant: I-SENS, INC., Seoul (KR)

(72) Inventors: In Jun Yoon, Seoul (KR); Jae Ho Shin, Seoul (KR); Yeon Ho Jung, Gyeonggi-do (KR); Geun Sig Cha, Seoul (KR); Hakhyun Nam, Seoul (KR)

(73) Assignee: I-SENS, INC., Seoul (KR)

(*) Notice: Subject to any disclaimer, the term of this patent is extended or adjusted under 35 U.S.C. 154(b) by 512 days.

(21) Appl. No.: 15/533,333

(22) PCT Filed: Dec. 31, 2015

(86) PCT No.: PCT/KR2015/014582
§ 371 (c)(1),
(2) Date: Jun. 5, 2017

(87) PCT Pub. No.: WO2016/108671
PCT Pub. Date: Jul. 7, 2016

(65) Prior Publication Data
US 2017/0350850 A1    Dec. 7, 2017

(30) Foreign Application Priority Data

Dec. 31, 2014  (KR) .................. 10-2014-0195173

(51) Int. Cl.
*G01N 27/416* (2006.01)
*G01N 27/327* (2006.01)
(Continued)

(52) U.S. Cl.
CPC ......... *G01N 27/416* (2013.01); *C07D 401/04* (2013.01); *C07F 15/002* (2013.01);
(Continued)

(58) Field of Classification Search
CPC .... G01N 27/416; G01N 33/66; G01N 27/327; C12Q 1/006; C12Q 1/004; C07F 15/002; C07D 401/04; C12M 1/40
See application file for complete search history.

(56) References Cited

U.S. PATENT DOCUMENTS

2003/0106810 A1\* 6/2003 Douglas ................. C12Q 1/001
 205/777.5
2012/0065614 A1 3/2012 Omary et al.

FOREIGN PATENT DOCUMENTS

JP 2003-503728 A 1/2003
JP 2014-089096 A 5/2014
(Continued)

OTHER PUBLICATIONS

W. Shen, et al. "An electrodeposited redox polymer-laccase composite film for highly efficient four-electron oxygen reduction" Journal of Power Sources, 226, p. 27-32, Mar. 2013.\*
(Continued)

*Primary Examiner* — J. Christopher Ball
(74) *Attorney, Agent, or Firm* — Conley Rose, P.C.

(57) ABSTRACT

The present disclosure relates to an electron transfer mediator comprising the osmium complex or a salt thereof, a reagent composition for an electrochemical biosensor, and an electrochemical biosensor, where the osmium compound or its salt maintains a stable oxidation-reduction form for an extended time period, a capacity to react with oxidoreductase being capable of performing the redox reaction of the target analytes, and no effect of oxygen partial pressure.

18 Claims, 17 Drawing Sheets

(51) Int. Cl.
  *C12M 1/40*   (2006.01)
  *G01N 33/66*  (2006.01)
  *C07D 401/04* (2006.01)
  *C07F 15/00*  (2006.01)
  *C12Q 1/00*   (2006.01)

(52) U.S. Cl.
  CPC .............. *C12M 1/40* (2013.01); *C12Q 1/004* (2013.01); *C12Q 1/006* (2013.01); *G01N 27/327* (2013.01); *G01N 33/66* (2013.01)

(56) References Cited

FOREIGN PATENT DOCUMENTS

| KR | 10-2011-0033874 A | 3/2011 |
| KR | 10-2012-0023208 A | 3/2012 |
| KR | 10-1239381 B1 | 3/2013 |
| WO | 2008007277 | 1/2008 |

OTHER PUBLICATIONS

P.A. Lay, et al. ("Cis-Bis (2, 2'-Bipyridine-N, N') Complexes of Ruthenium (III)/(II) and Osmium (III)/(II)", Inorganic Syntheses, vol. 24, pp. 291-299, Jan 1986.*

European Search Report for 15875765.8 dated May 4, 2018 (7 pages).

Nieh, Chi-Hua, et al., Electrostatic and steric interaction between redox polymers and some flavoenzymes in mediated bioelectrocatalysis, Journal of Electroanalytical chemistry (2013), 689:26-30.

International Patent Application No. PCT/KR2015/014582, International Search Report dated Apr. 21, 2016 (7 pages).

Jenkins, Peter et al., "A Mediated Glucose/oxygen Enzymatic Fuel Cell based on Printed Carbon Inks Containing Aldose Dehydrogenase and Laccase as Anode and Cathode," Enzyme and Microbial Technology, 2012, vol. 50, pp. 181-187.

Jenkins, Peter et al., "Evaluation of Performance and Stability of Biocatalytic Redox Films Constructed with Different Copper Oxygenases and Osmium-Based Redox Polymers," Bioelectrochemistry, 2009, vol. 76, pp. 162-168.

Conghaile, Peter O. et al., "Mediated Glucose Enzyme Electrodes by Cross-linking Films of Osmium Redox Complexes and Glucose Oxidase on Electrodes," Analytical and Bioanalytical Chemistry, 2013, vol. 405, pp. 3807-3812.

* cited by examiner

[Fig. 1]
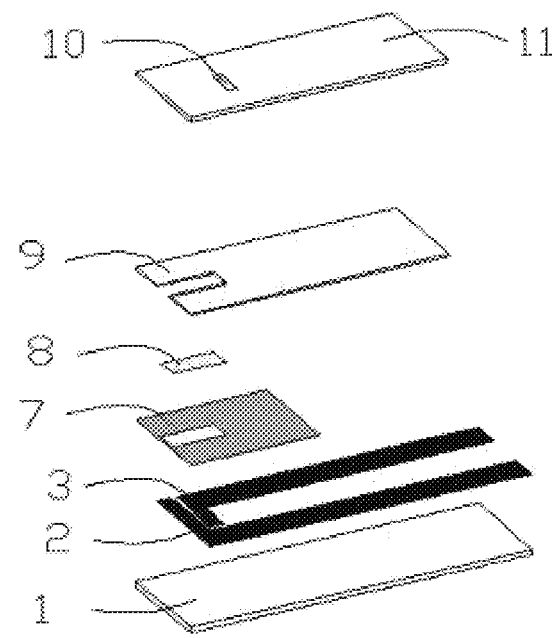
[Fig. 2]
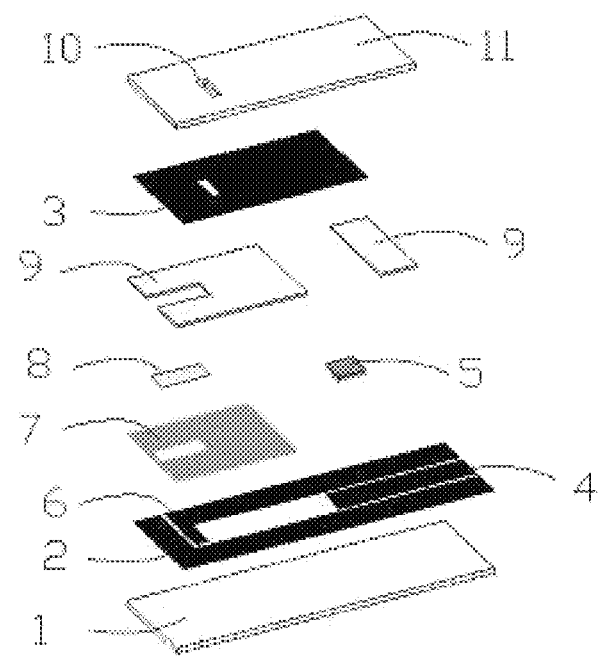

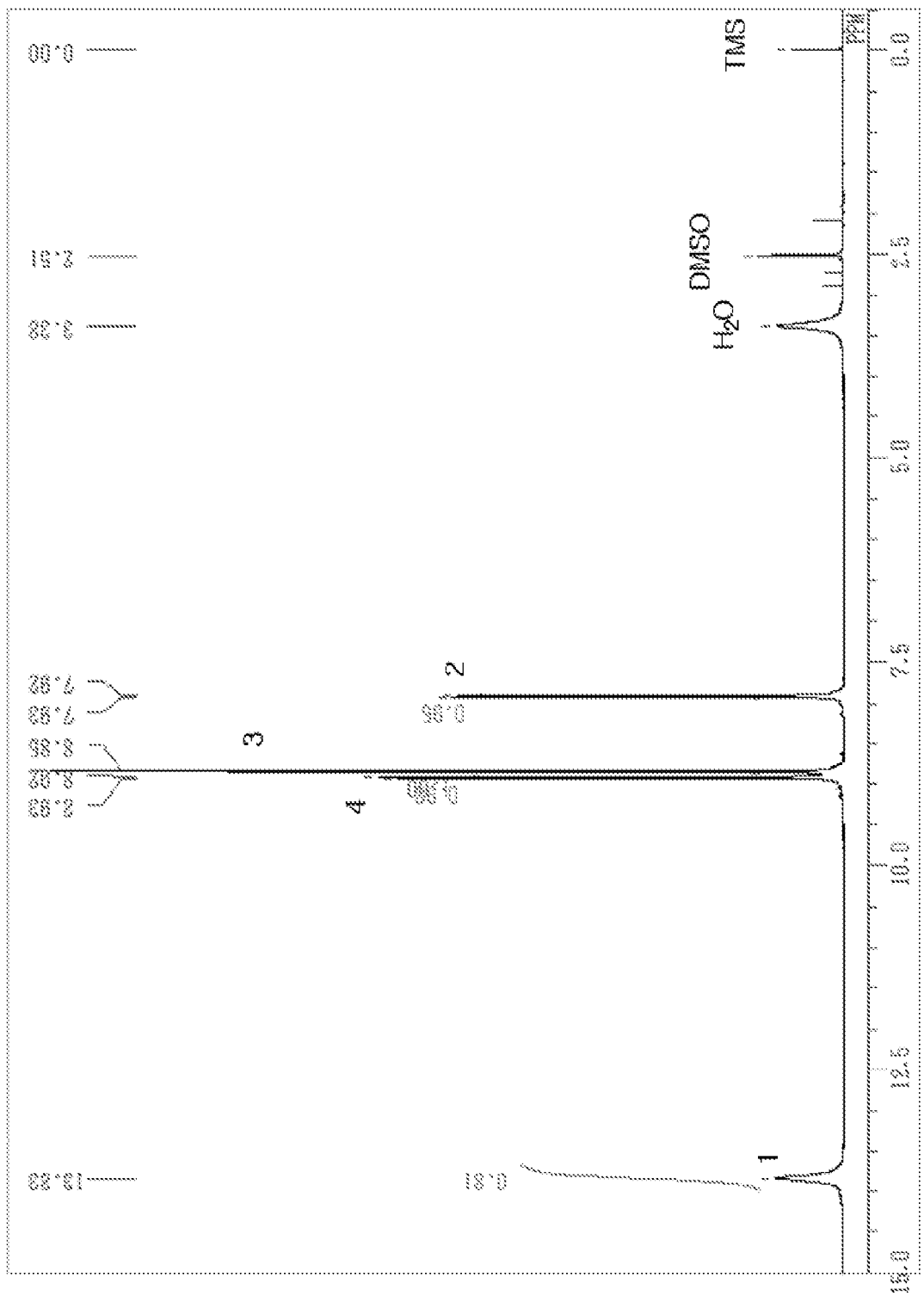

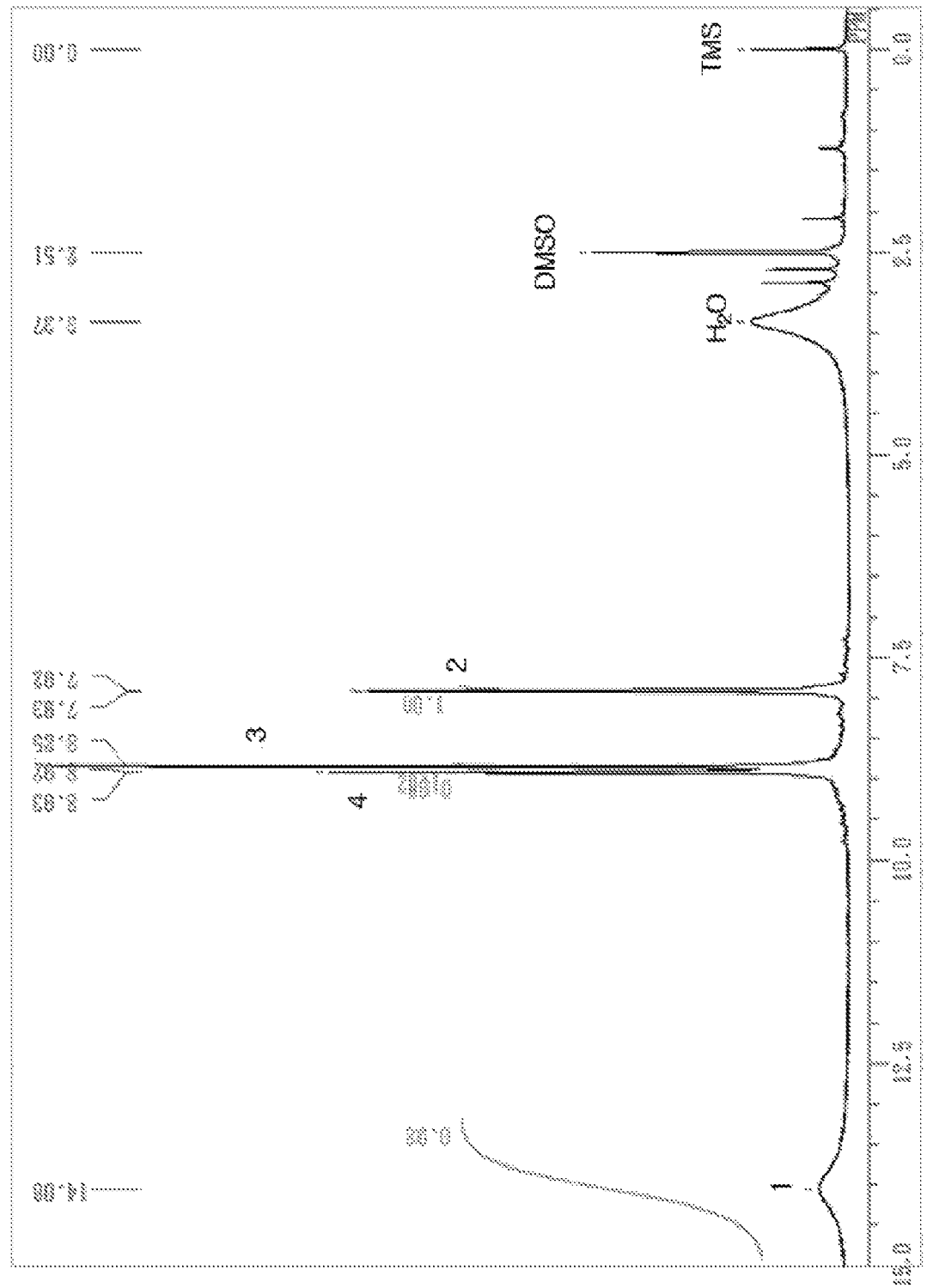

【Fig. 4a】
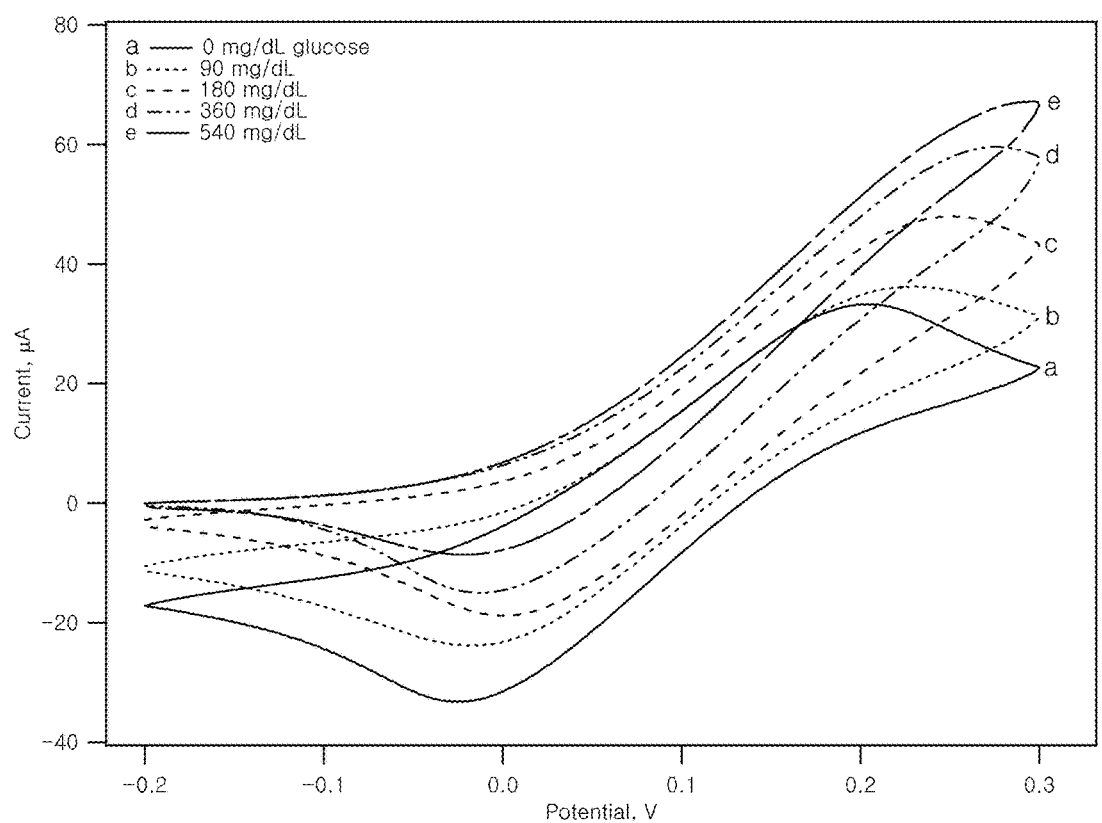
【Fig. 4b】
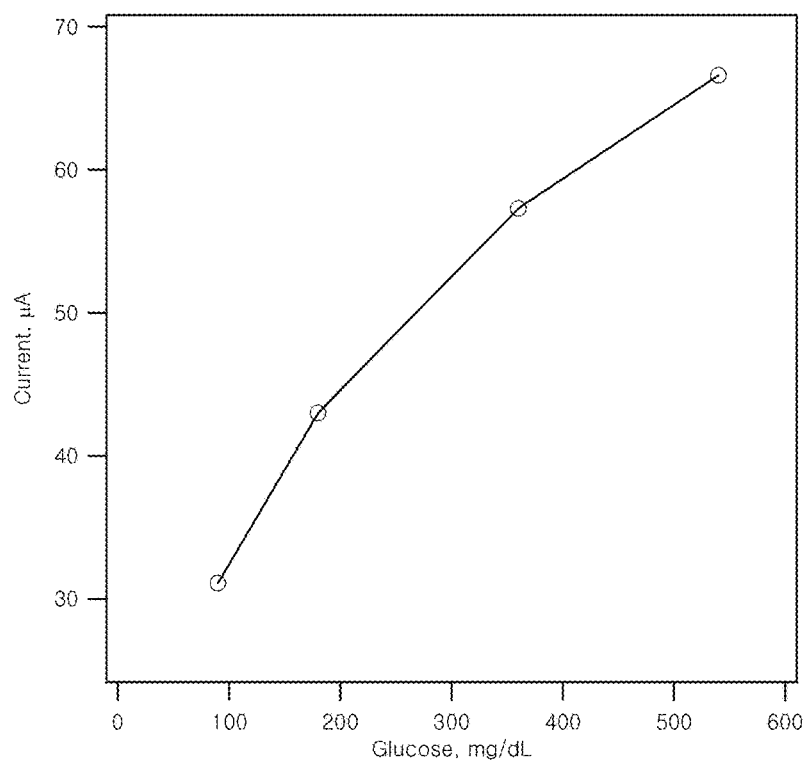

[Fig. 5a]
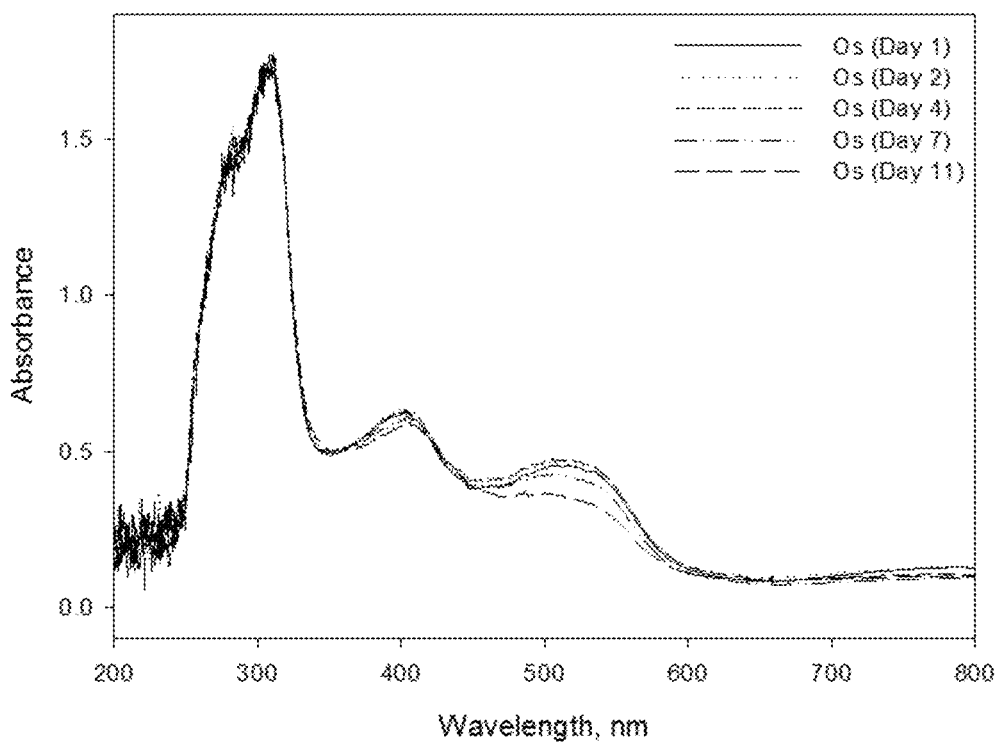
[Fig. 5b]
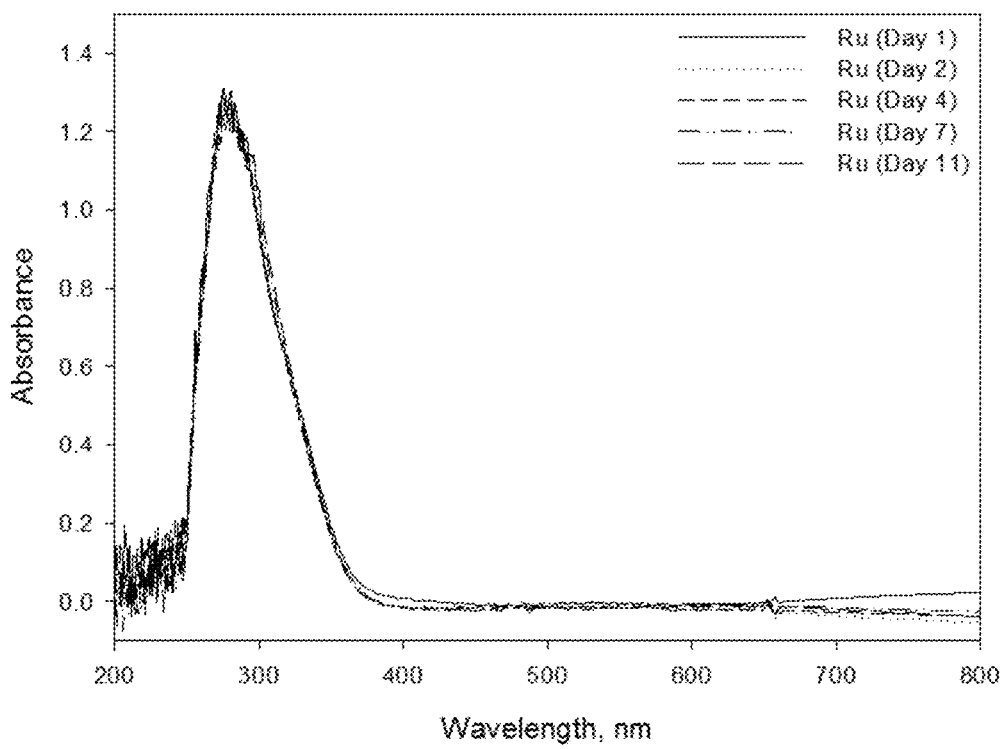

[Fig. 5c]
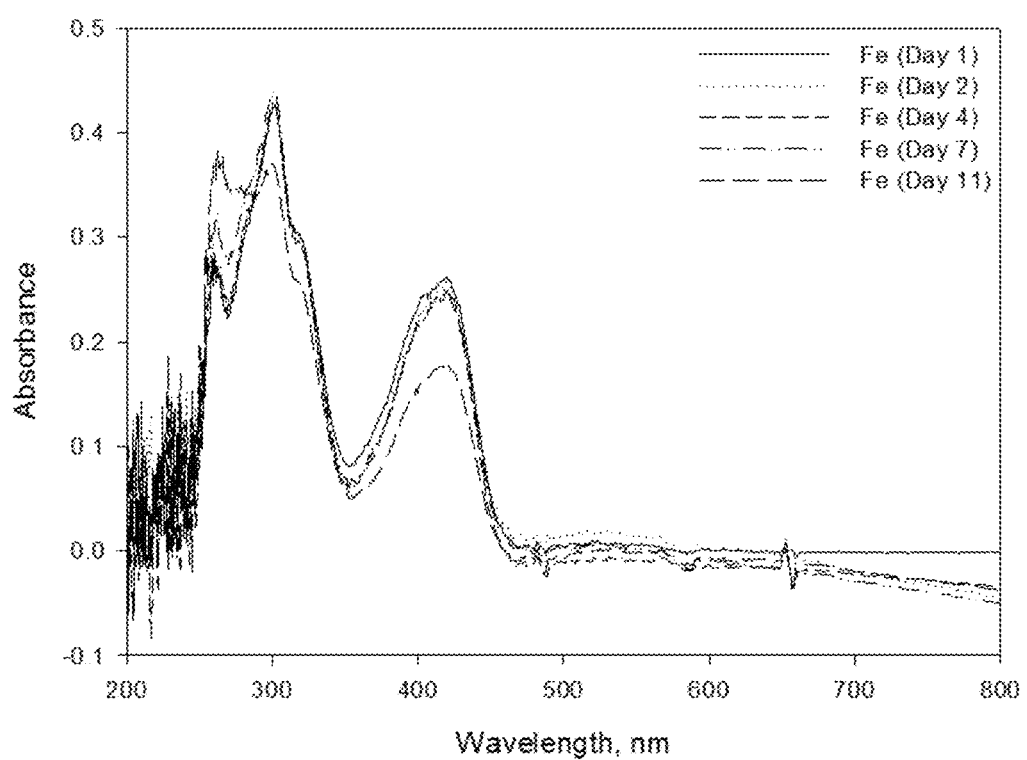

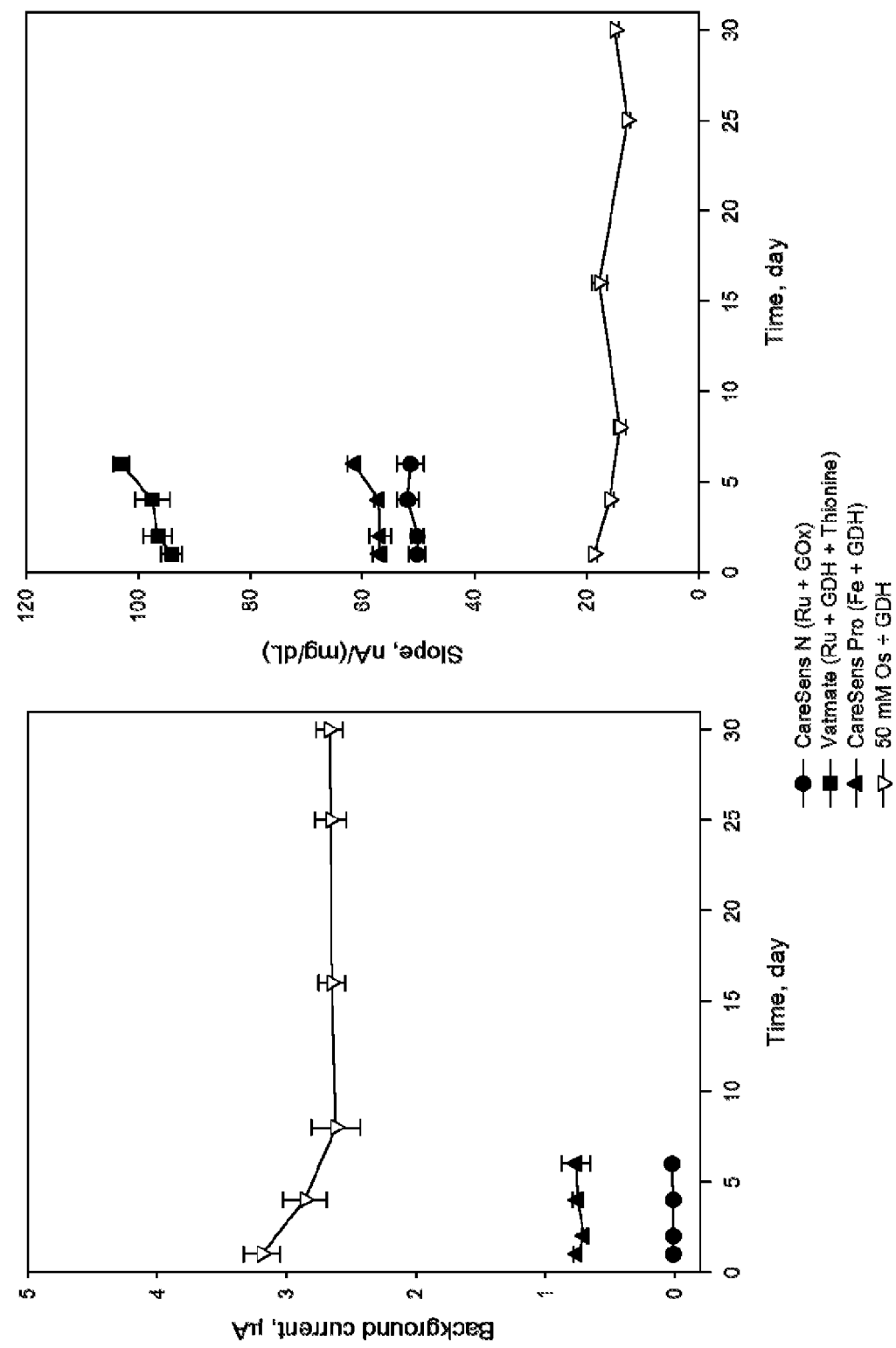
[Fig. 6]

[Fig. 7]
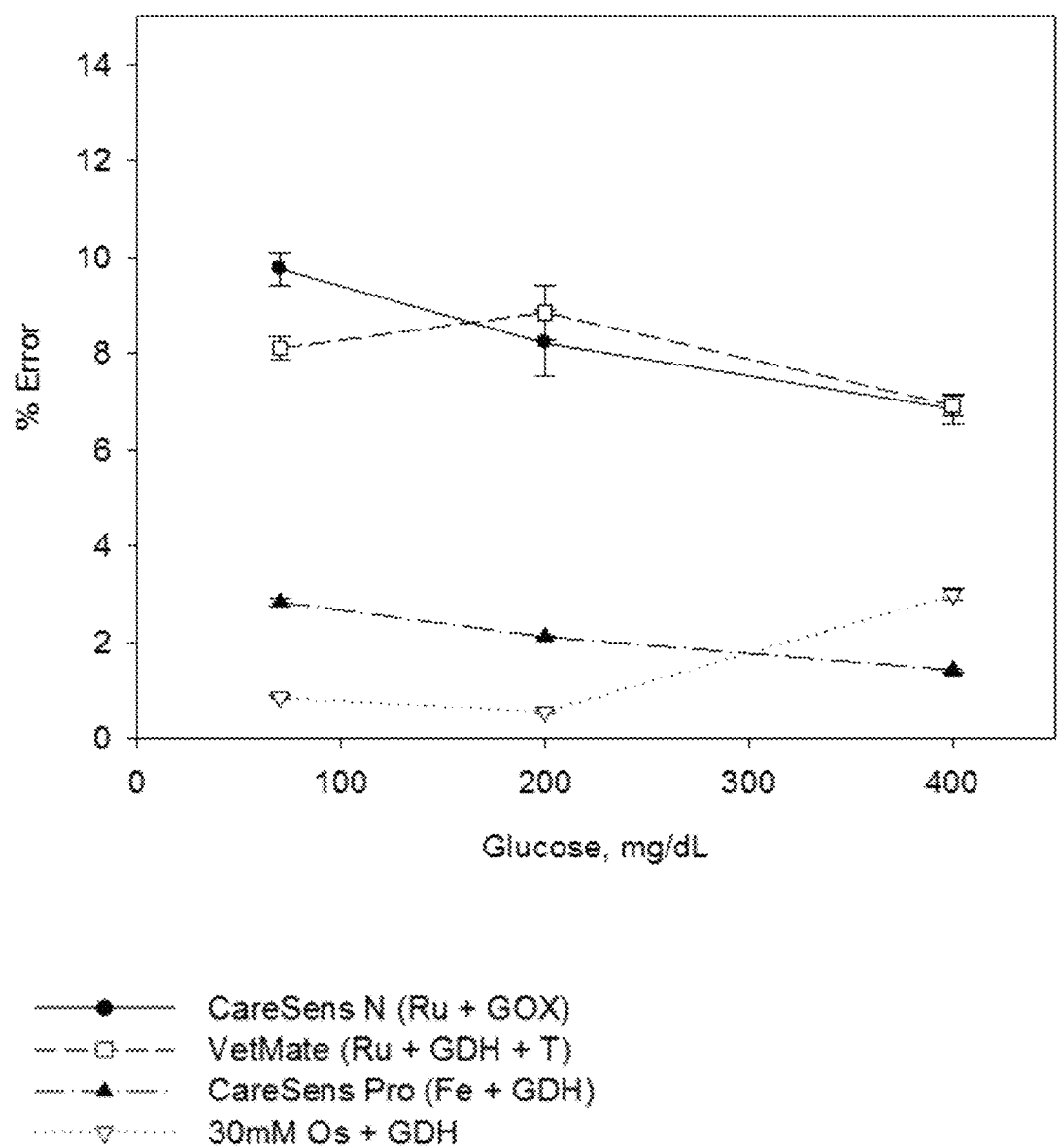

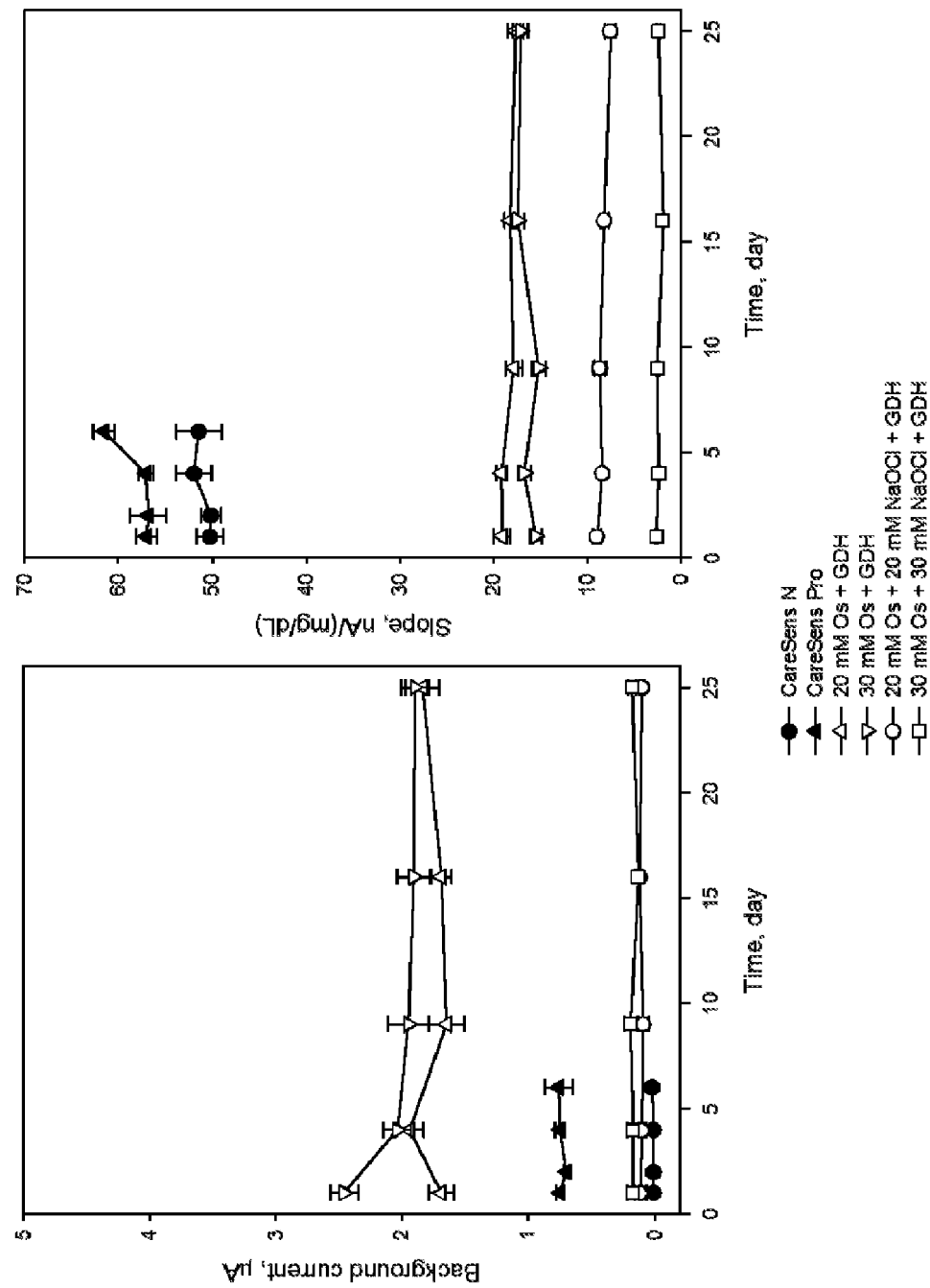
[Fig. 8]

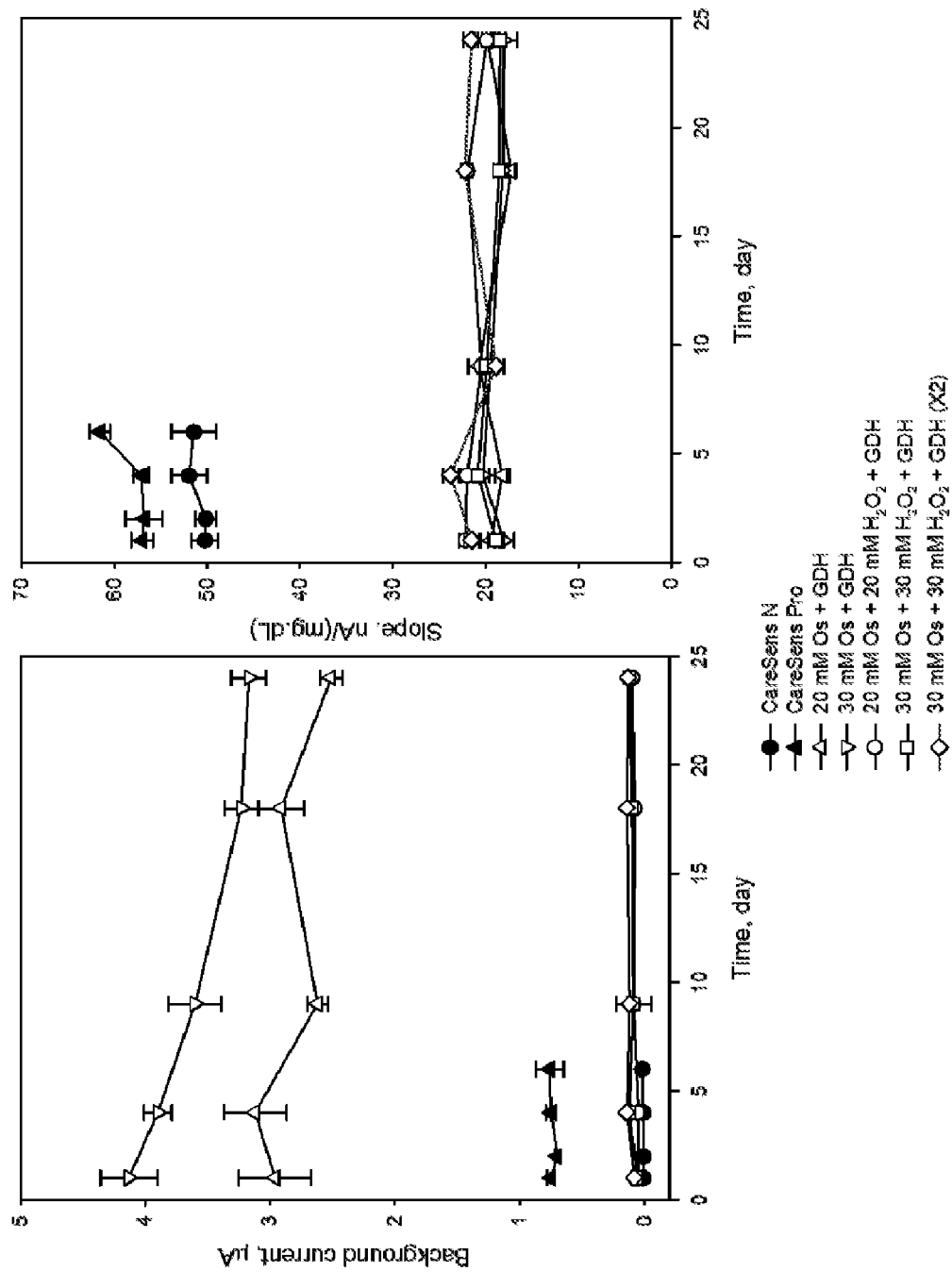
[Fig. 9]

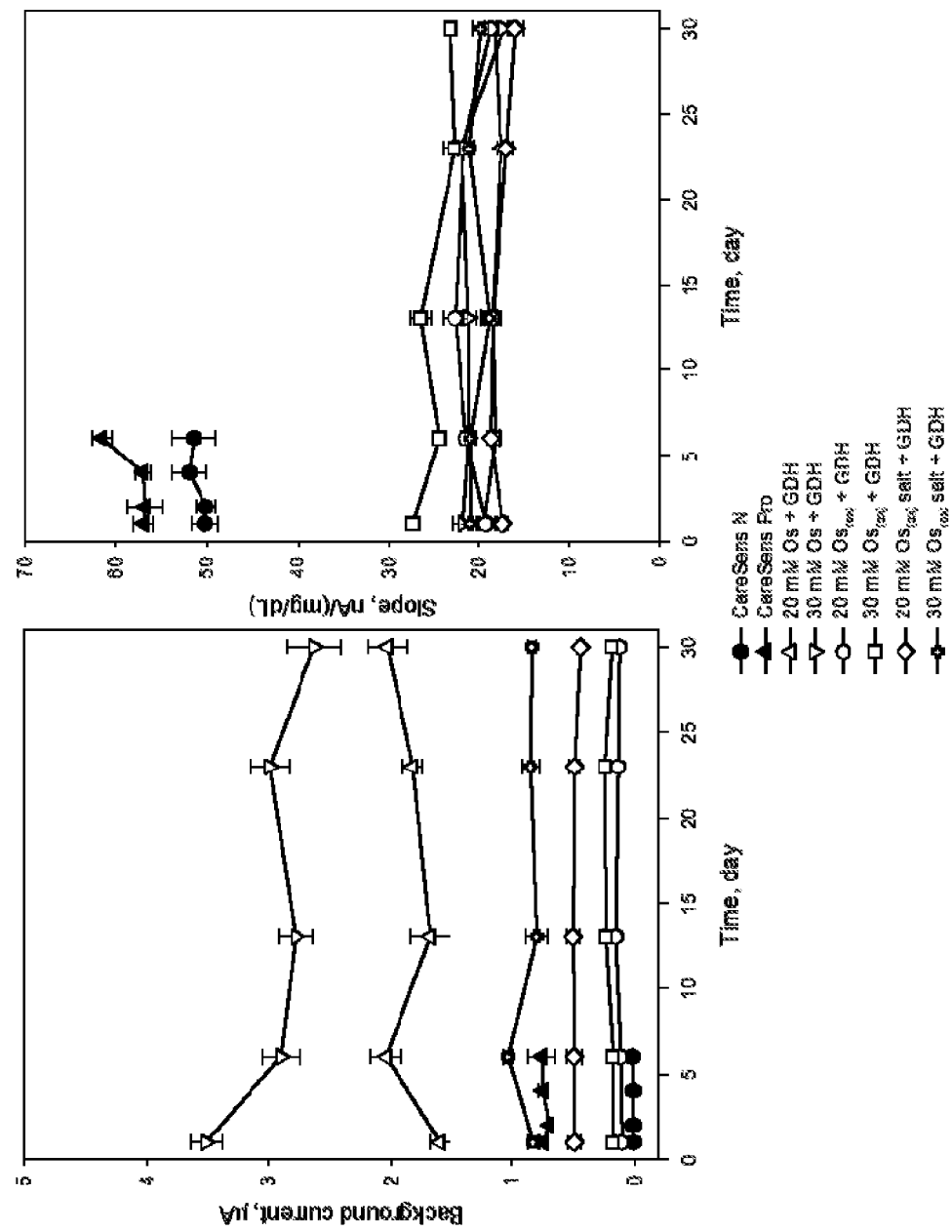
[Fig. 10]

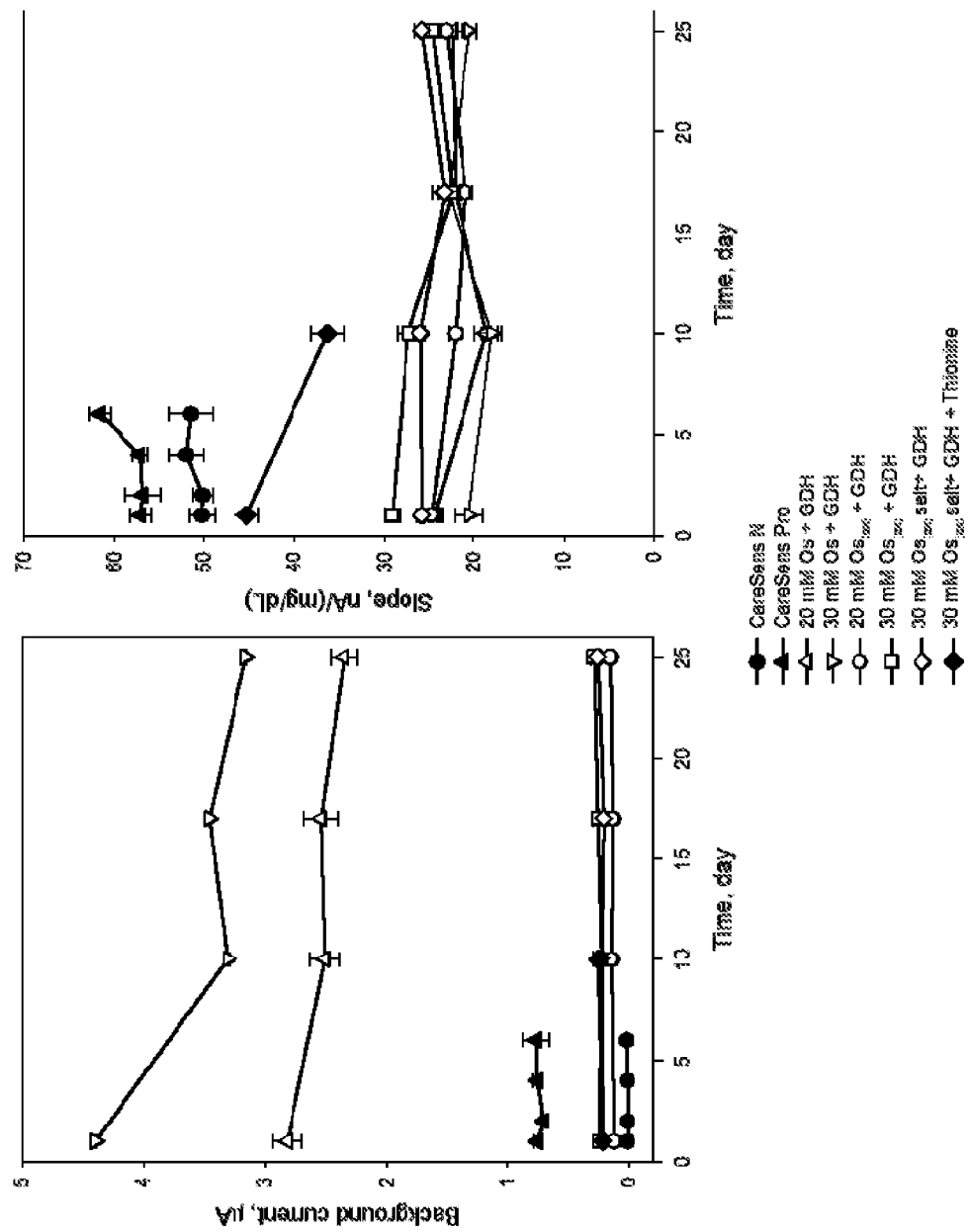
[Fig. 11]

[Fig. 12]
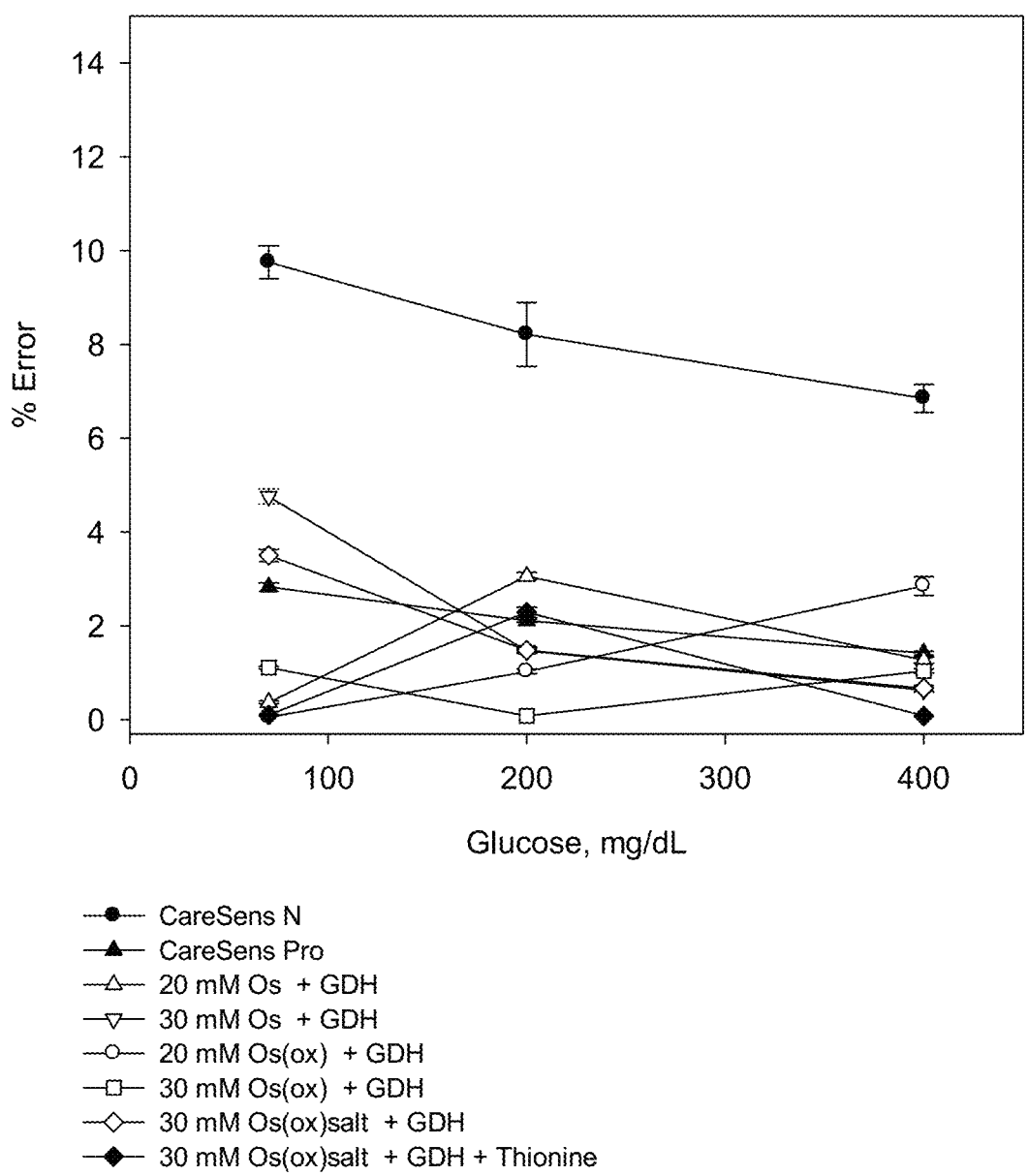

[Fig. 13a]
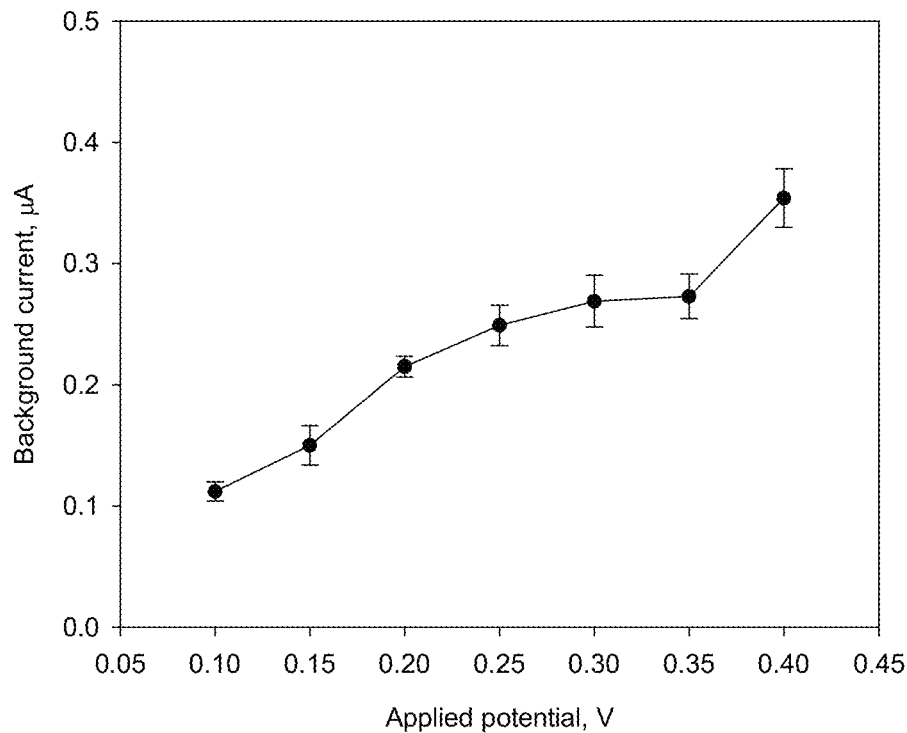
[Fig. 13b]
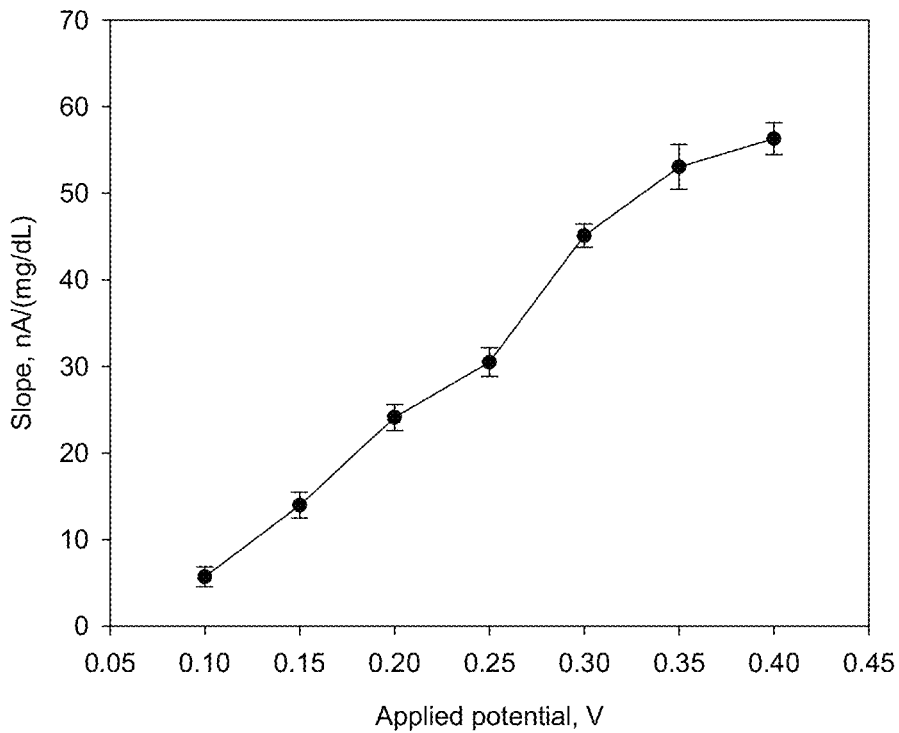

【Fig. 14a】
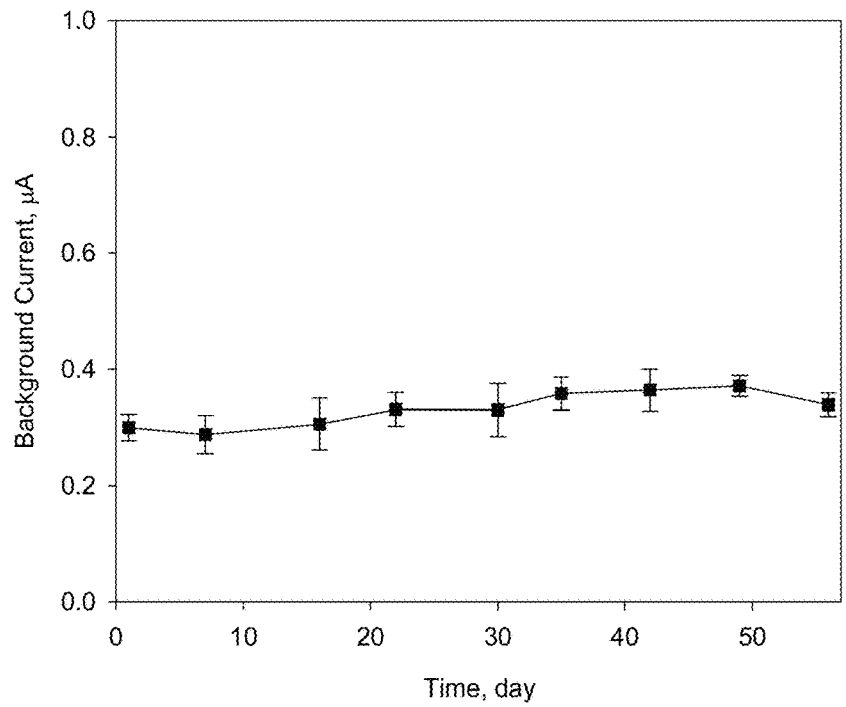
【Fig. 14b】
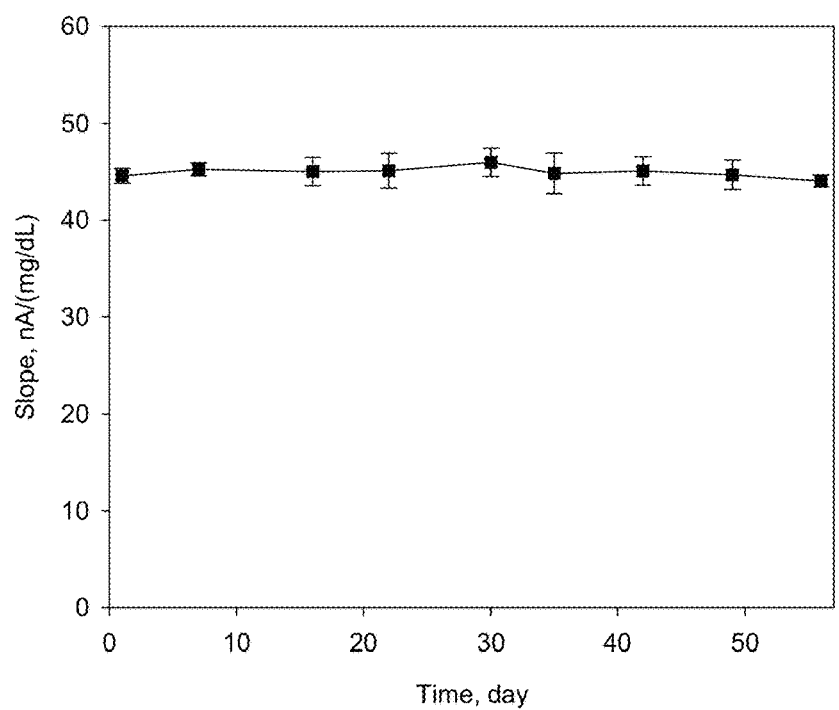

[Fig. 15a]
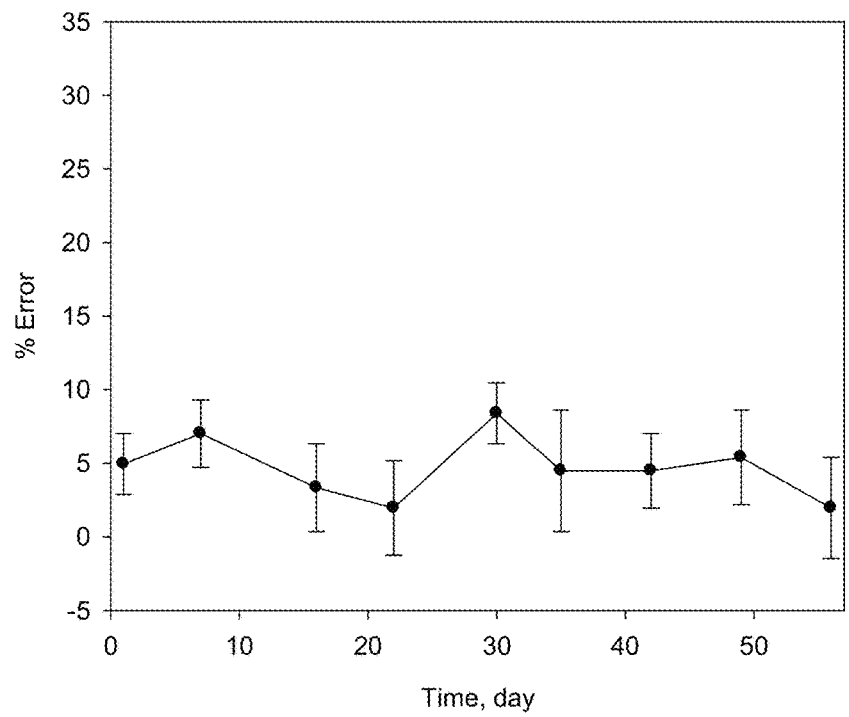
[Fig. 15b]
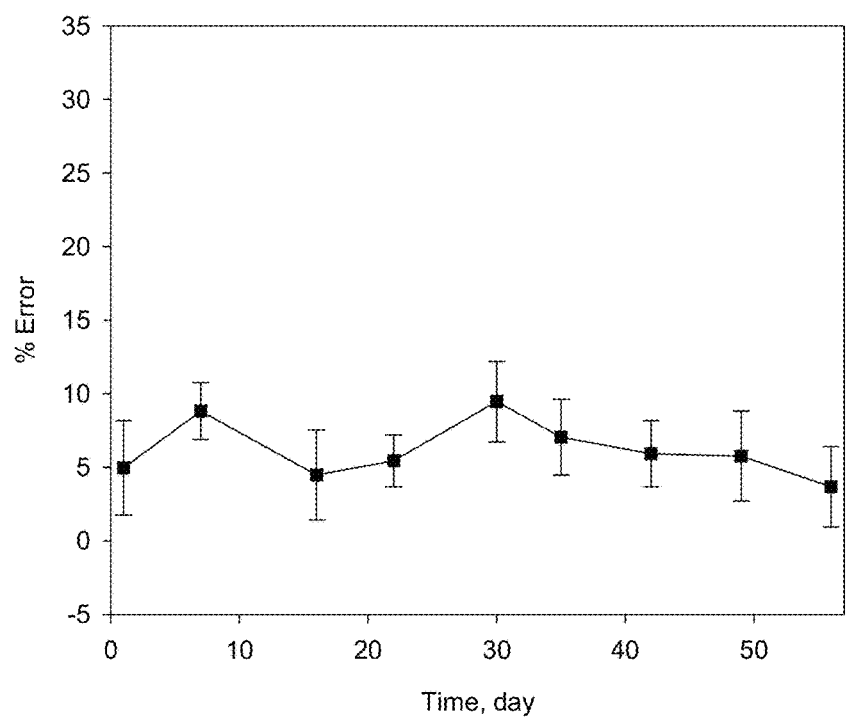

[Fig. 16]
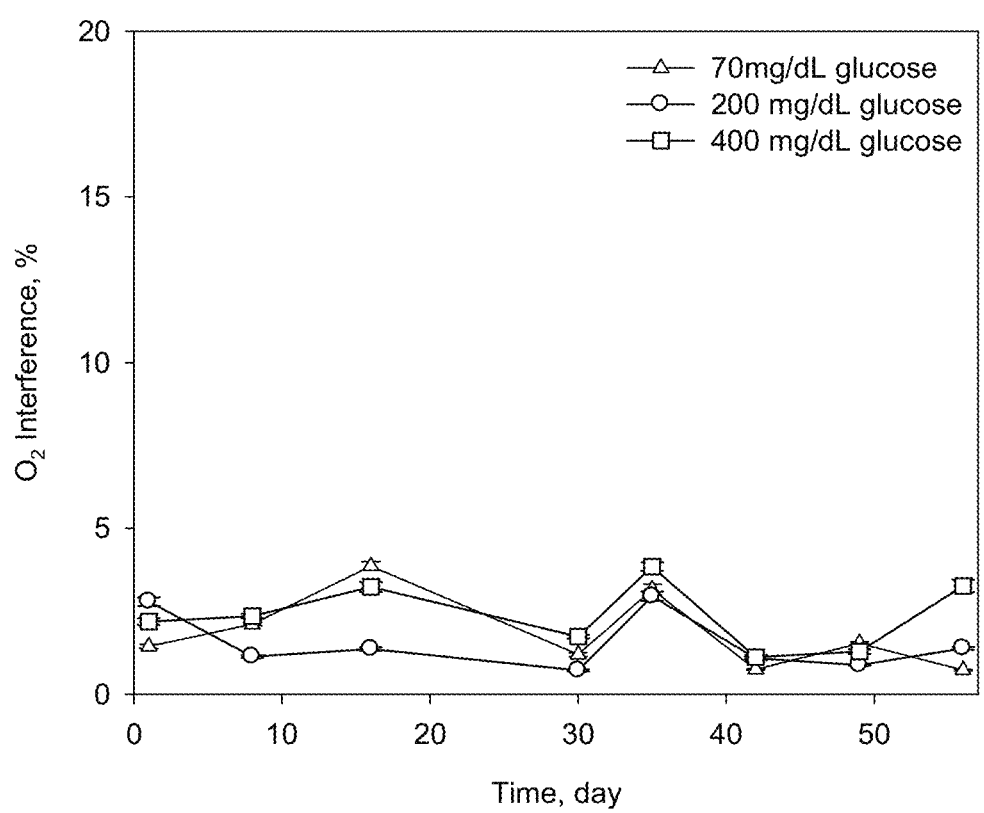

ELECTROCHEMICAL BIOSENSOR

CROSS-REFERENCE TO RELATED APPLICATIONS

This application is a 35 U.S.C. § 371 national stage application of PCT/KR2015/014582 filed on Dec. 31, 2015, which claims priority to Korean Patent Application No. 10-2014-0195173 filed on Dec. 31, 2014, both of which are incorporated by reference herein in their entireties for all purposes.

STATEMENT REGARDING FEDERALLY SPONSORED RESEARCH

Not applicable.

TECHNICAL FIELD

The present disclosure relates to an osmium complex which may not be affected by oxygen partial pressure and which stably retains its redox state for a long time, and an electron transfer mediator including an osmium complex, and an electrochemical biosensor comprising the electron transfer mediator and an oxidoreductase.

BACKGROUND OF DISCLOSURE

The development of biosensors has been of interested for quantitative and qualitative analysis of target analytes from the medical field (such as blood sugar sensors), the environment and foods.

Biosensors may use an enzyme as a chemical sensor for selectively detecting and measuring a chemical substance in a sample, using a biological sensing function in which an organism such as a microorganism or a functional substance in an organism reacts sensitively with a specific substance. The biosensors may be useful for medical measurement, such as blood sugar sensor, as well as in the fields of food engineering and environmental measurement.

Periodic measurement of blood glucose is very important in diabetes management, and a wide variety of electrochemical biosensors with accuracy and precision are widely used for measurement of blood glucose. An electrochemical biosensor for measuring blood glucose is prepared by coating a reagent prepared by mixing an enzyme, an electron transfer mediator, various stabilizers and a dispersing agent, to a working electrode and drying it. The kind of the enzyme and the property of electron transport mediators influence the characteristics of the biosensor.

For example, FAD-GOx (flavin adenine dinucleotide-glucose oxidase), a glucose oxidase reductase used in most commercial electrochemical sensors, is thermally stable and has excellent reaction selectivity to oxidize only glucose. However, because of FAD-GOx reacts with oxygen dissolved in blood, sensors adopting FAD-GOx enzymes can produce a very different measurement result depending on the type of blood sample, such as venous, arterial, or capillary blood.

The prior art has proposed a method of measuring generated hydrogen peroxide. When an oxidation potential of about +600 mV (vs. Ag/AgCl) is introduced into the electrode, the current value is obtained, but the glucose sensor adopted in this method is highly dependent on the amount of dissolved oxygen in the sample. By applying a high oxidation potential when measuring the oxidation current of hydrogen peroxide, the drug and metabolites (ascorbic acid, uric acid, acetaminophen, dopamine, and etc.) being capable of oxidized in a low potential are oxidized together at the electrodes, thereby causing severe measurement errors.

As one of the methods to overcome the oxygen dependency of the glucose sensor, an electron transfer mediator instead of oxygen was introduced to facilitate the electron transfer between the electrode surface and the enzyme active site on the electrode surface, and organometallic electron transfer mediator (such as Ferrocene derivatives) which have a relatively low potential were thus introduced to minimizing the interference effect of other oxidative substances (ascorbic acid, uric acid, acetaminophen, dopamine, and etc.)

The development trend of blood glucose sensors has therefore changed into the use of GDH, requiring no oxygen in the enzymatic reaction, in order to block changes in measured values due to differences in oxygen partial pressure (pO2), instead of GOx including oxygen involved in the enzymatic reaction with the blood glucose. In addition, electron transfer mediators, organic such as quinone derivatives (phenanthroline quinone, Quineonediimine etc.) and organometallic compounds such as Ru complexes (ruthenium hexamine, etc.) or osmium complexes replace the Ferricyanide having low stability to temperature and humidity have been developed.

A common electron transfer medium is potassium Ferricyanide [$K_3Fe(CN)_6$]. Because it is inexpensive and has a good reactivity, it can be useful for all sensors using FAD-GOx, PQQ-GDH or FAD-GDH. However, the sensor using the above-mentioned electron transfer mediator has a measurement error caused by the interfering substance such as uric acid or gentisic acid in the blood and is easily deteriorated due to temperature and humidity. Thus, it must be carefully prepared and stored. However, it does not accurately detect glucose at a low concentration due to a change in background current after long storage.

Hexamine ruthenium chloride [$Ru(NH_3)_6Cl_3$] has higher redox stability than the Ferricyanide. Biosensors using hexamine ruthenium chloride as an electron transfer medium has advantages in manufacturing and storage and has stability due to small change of background current even when it is stored for a long time. However, it cannot match the reactivity of FAD-GDH, when it is used with FAD-GDH, and thus, it cannot be manufactured as a commercial product. Also, this electron transfer medium is not accurate because the sensor strip is affected by the oxygen partial pressure.

Therefore, there is still a need to develop a reagent for reduction-oxidation reaction, specifically for electrochemical biosensor that is no influenced by oxygen, has little change in performance due to temperature and humidity, has little change in performance even after storage for a long period of time, can measure a wide range of concentration, and/or is suitable for mass production.

SUMMARY OF DISCLOSURE

An embodiment of the present disclosure provides an osmium complex, its salt compound and a method of preparation thereof, where the compound or its salt is an electron transfer mediator for an electrochemical biosensor, because the compound or its salt maintains a stable oxidation-reduction form for an increased time and has a capacity to react with oxidoreductase without an effect of oxygen partial pressure.

In still another embodiment, a reagent composition for a redox reaction comprising an electron transfer mediator comprising the osmium complex or a salt thereof is provided.

In another embodiment, an electrochemical biosensor comprising an electron transfer mediator comprising an osmium complex or a salt thereof is described herein.

The present disclosure further relates to an osmium complex or a salt thereof, an electron transfer mediator comprising the osmium complex or a salt thereof, a reagent composition for redox reaction, an electrochemical biosensor, for example a glucose sensor, wherein the compound or its salt has a stable oxidation-reduction form for an increased or extended time and a capacity to react with oxidoreductase being capable of performing the redox reaction of the analytes in the biological sample without an effect of oxygen partial pressure.

Specifically, the present disclosure relates to an osmium complex or a salt thereof, and a preparation method thereof, where the osmium complex or a salt thereof has a stable oxidation-reduction form for an extended or a long time and a capacity to react with oxidoreductase being capable of performing the redox reaction of the analyte in the biological sample without an effect of oxygen partial pressure.

In an embodiment, the present disclosure relates to an electron transfer mediator comprising the osmium complex or its salt which has a stable oxidation-reduction form, which is maintained for an extended time, and a capacity to react with oxidoreductase being capable of performing the redox reaction of the analytes in the biological sample without an effect of oxygen partial pressure. The osmium complex is represented by the following Chemical Formula 1.

Os(A)$m$X$n$      Chemical Formula 1:

Wherein,
A is a compound represented by the following Chemical Formula 2,

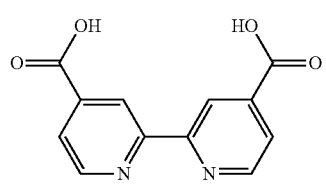

Chemical Formula 2

X is independently halogen, for example at least one species selected from the group consisting of F, Cl, Br and I, m is an integer of 1 to 3, n is an integer of 0 to 4, and a sum of m and n is an integer of 3 to 5.

Embodiments of the reagent for reduction-oxidation reactions, specifically for electrochemical biosensors, have no effect of oxygen partial pressure, little change in performance due to temperature and humidity, little change in performance even after storage for a long period of time, can measure a wide range of concentration, and/or are suitable for mass production.

An embodiment of the present disclosure relates to an electrochemical biosensor, which is prepared by immobilizing an osmium complex or its salt represented by Chemical Formula 1 and an enzyme performing the redox reaction of analytes in liquid biological sample on at least two electrodes. The examples of the electrodes are a working electrode and an auxiliary electrode, for example, where the osmium complex or its salt and the enzyme are immobilized on the working electrode.

In one embodiment, although a biosensor for measuring glucose is presented as an example of the applicable electrochemical biosensor, the present disclosure can be applied to a biosensor for quantitative determination of various substances such as cholesterol, lactate, creatinine, hydrogen peroxide, alcohol, amino acid and glutamate, by changing the types of enzymes contained in the reagent composition of the present disclosure.

The long-term stability of a glucose strip sensor including the osmium complex in an oxidative state, with applied voltage 0.3V under storage conditions were tested. As a result, the background signal (0.3 μA), response slope (45 nA/(mg/dL)) and error percentage (%) depending on the oxygen partial pressure (at most 4%) are stably maintained for 8 weeks or longer. On the basis of the result of calibrating in 20 mM to 200 mM, the error percentage (%) calculated by using the current value of 70 mg/dL glucose and 100 mg/dL glucose over time shows a significant result of 10% or lower. The effect of oxygen partial pressure which is most serious problem of conventional sensors was evaluated as 4% or lower.

BRIEF DESCRIPTION OF DRAWINGS

Reference numerals used in drawings pertain to: 1: substrate; 2: working electrode; 3: auxiliary electrode; 4: lead of auxiliary electrode; 5: circuit connection ground; 6: flow sensing electrode; 7: Insulating plate; 8: reagent composition for redox reaction; 9: Fitting plate; 10: vent; and 11: upper plate.

FIG. 2 is an exploded skew drawing of face-to-face (sandwich-type) biosensor in accordance with an embodiment of the present invention.

FIG. 3a and FIG. 3b are the result of 1H NMR spectrum analysis for the osmium compound obtained in Example 1.

FIG. 4a and FIG. 4b are grapes showing the measurement current according to the change in the glucose concentration in Example 1.

FIG. 5a to FIG. 5c are the comparison of change in UV-visible light spectrum according to various electron transfer mediators in an aqueous solution with time change; FIG. 5a for osmium complex, FIG. 5b for ruthenium hexamine and FIG. 5c for Ferricyanide.

FIG. 6 shows the change in the characteristics of the osmium complex-based glucose strip sensor over time in the storage conditions; (a) background current and (b) response slope.

FIG. 7 is a comparison of interference result caused by oxygen partial pressure for the Os-based glucose strip sensor over time, depending on the glucose concentration.

FIG. 8 shows the change in the characteristics of the osmium complex-based glucose strip sensor over time in the storage conditions, after the addition of oxidizing agent (NaOCl); (a) background current and (b) response slope.

FIG. 9 shows the change in the characteristics of the osmium complex-based glucose strip sensor over time in the storage conditions, after the addition of oxidizing agent ($H_2O_2$).

FIG. 10 shows the change in the characteristics of the osmium complex-based glucose strip sensor over time in the storage conditions, where the osmium complex (oxidized state) was obtained by oxidizing with oxidizing agent ($H_2O_2$).

FIG. 11 shows the change in the characteristics of the osmium complex-based glucose strip sensor over time in the storage conditions, where the osmium complex (oxidized state) was obtained by oxidizing with oxidizing agent (NaOCl).

FIG. 12 is a comparison of interference result caused by oxygen partial pressure for the osmium complex-based glucose strip sensor over time, depending on the glucose concentration, where the osmium complex (oxidized state) was obtained by oxidizing with oxidizing agent (NaOCl).

FIG. 13a and FIG. 13b are shows the change in the characteristics of the osmium complex-based glucose strip sensor depending on the applied voltage, where the osmium complex (oxidized state) was obtained by oxidizing with oxidizing agent (NaOCl).

FIG. 14a and FIG. 14b show the change in the characteristics of the osmium complex (oxidized state)-based glucose strip sensor over time in the storage conditions.

FIG. 15a and FIG. 15b show the change in the error % of the osmium complex (oxidized state)-based glucose strip sensor over time in the storage conditions, depending on the glucose concentration.

FIG. 16 is a comparison of interference result caused by oxygen partial pressure for the osmium complex (oxidized state)-based glucose strip sensor over time, depending on the glucose concentration.

DETAILED DESCRIPTION OF THE DISCLOSURE

Hereinafter, the present disclosure will be described in more detail. An embodiment of the present disclosure relates to an electrochemical biosensor which is prepared by immobilizing an osmium complex or its salt represented by Chemical Formula 1 and an enzyme performing the redox reaction of analytes in liquid biological sample on at least two electrodes.

Os(A)$_m$X$_n$   Chemical Formula 1

Wherein,

A is a compound represented by Chemical Formula 2, that is, 4,4'-dicarboxy-2,2'-bipyridine (dcbpy),

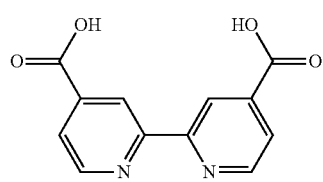

Chemical Formula 2

X is independently selected from the group consisting of halogen, for examples, one selected from the group consisting of F, Cl, Br and I, m is an integer of 1 to 3, n is an integer of 0 to 4, a sum of m and n is an integer of 3 to 5.

Examples of the osmium complexes include the compounds of Chemical Formula 3, Chemical Formula 4 and Chemical Formula 5.

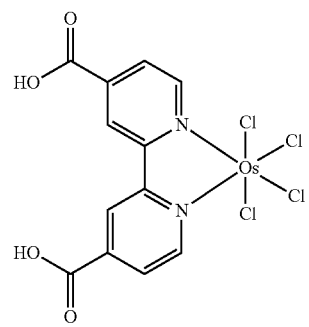

Chemical Formula 3

Os(dcbpy)Cl$_4$

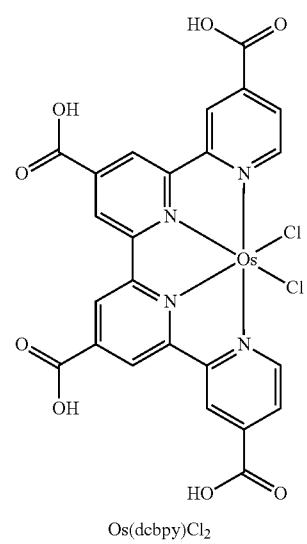

Chemical Formula 4

Os(dcbpy)Cl$_2$

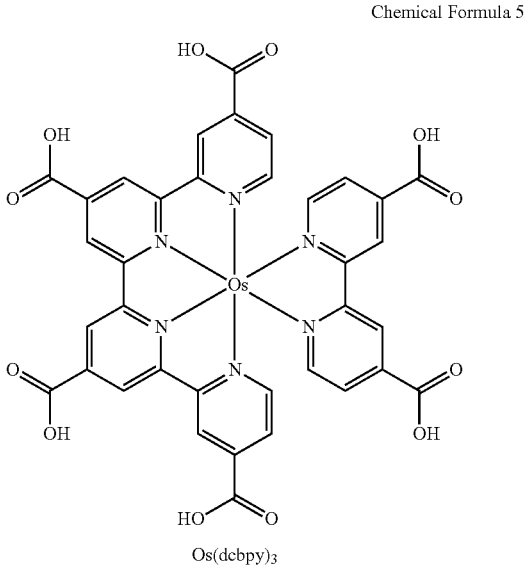

Chemical Formula 5

Os(dcbpy)$_3$

The osmium complex having the structure represented by the formula (1) may include a trivalent osmium complex and a divalent osmium complex, the osmium complex having the structure represented by the formula (1) may preferably be an oxidized compound (trivalent Os compound). In addition, when the osmium complex is a mixture containing both an oxidized state and a reduced state compound as an osmium complex represented by the general formula (1), the osmium complex in an oxidized state may be provided by the oxidative treatment, providing the oxidized osmium complex, or adding an oxidant to the reagent composition.

The osmium complex may be in a salt form, and in some embodiments may be more preferable since the salt compound has a high solubility. The salt compound may be a salt compound of at least one alkali metal selected from the group consisting of Li salt, Na salt, K salt, Rb salt, Cs salt and Fr salt.

Therefore, the osmium complex or its salts may be an osmium complex having the structure of Formula 1 or a salt thereof, and the osmium contained in the osmium complex or its salt is preferably in oxidation state, i.e., trivalent osmium. Specifically, after preparing an osmium complex or preparing a salt of an osmium complex, an osmium complex or its salt is treated by an oxidant to produce an osmium complex in an oxidized state, followed by changing the an osmium complex in an oxidized state into its salt.

In one embodiment, the osmium complex may be synthesized using a compound having the Chemical formula (2) and a compound represented by the following formula (6).

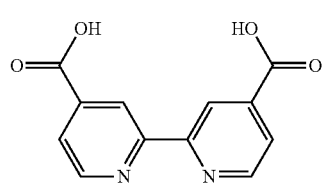

Chemical formula 2

Chemical formula 6 wherein,

Y is K, Na or $NH_4$, X is a halogen, p is an integer of 1 to 2, and q is an integer of 1 to 6.

In a specific embodiment, the osmium compound may be synthesized by using 4,4'-dicarboxy-2,2'-bipyridine (dcbpy) and the compound of Chemical Formula 6, for examples $K_2OsCl_6$ or $(NH_4)_2[OsCl_6]$ as a starting material. An example of preparing method of osmium compound, the procedure using dcbpy and $K_2OsCl_6$ is shown in Reaction Scheme 1.

Reaction Scheme 1

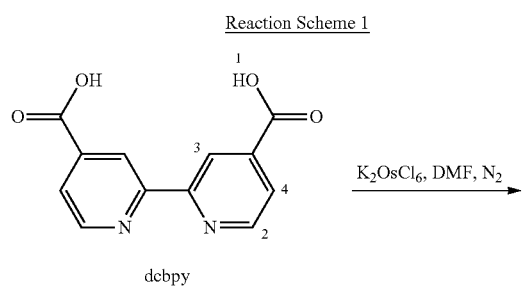

dcbpy

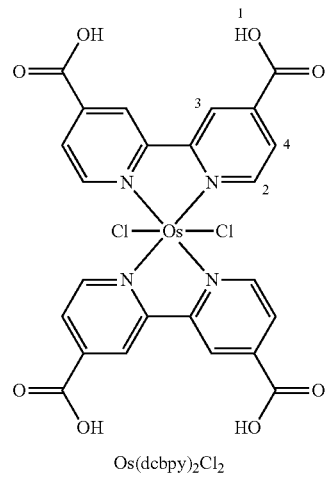

$Os(dcbpy)_2Cl_2$

The synthesized osmium complex may be the osmium complex in the oxidized state (trivalent Os compound) obtained by performing oxidation treatment on the synthesized osmium complex using various oxidizing agents. The oxidizing agent used in the oxidation treatment of the present invention is not particularly limited, but specific examples are NaOCl, $H_2O_2$, $O_2$, $O_3$, $PbO_2$, $MnO_2$, $KMnO_4$, $ClO_2$, $F_2$, $Cl_2$, $H_2CrO_4$, $K_2Cr_2O_7$, $N_2O$, $Ag_2O$, $OsO_4$, $H_2S_2O_8$, pyridinium chlorochromate, and 2,2'-Dipyridyldisulfide. According to an embodiment of the present invention, the compound in oxidation state can be prepared according to the following Reaction Scheme 2.

Reaction Scheme 2

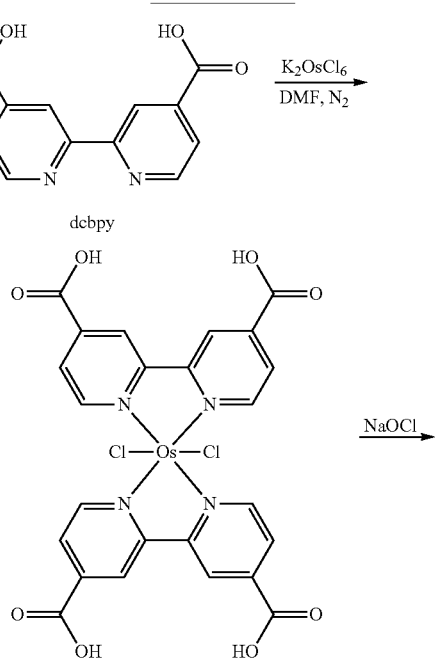

$Os(dcbpy)_2Cl_2 = Os(II/III)$

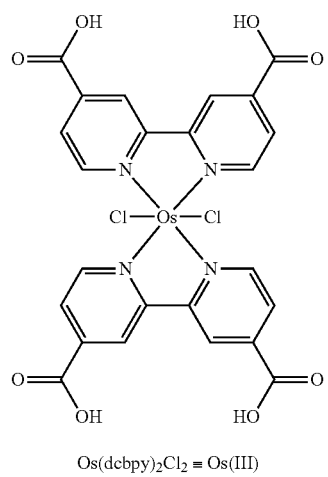

Os(dcbpy)₂Cl₂ ≡ Os(III)

In accordance with one embodiment, the salt form of the osmium complex is more preferred because of the increased solubility. As an example of preparing a salt of an osmium complex, a process for preparing a salt compound of an osmium complex using NaOH is shown in the following reaction scheme (3). The salt compound of the osmium complex may be a salt of at least one alkali metal selected from the group consisting of Li salt. Na salt. K salt. Rb salt. Cs salt and Fr salt, but is not limited thereto.

Reaction Scheme 3

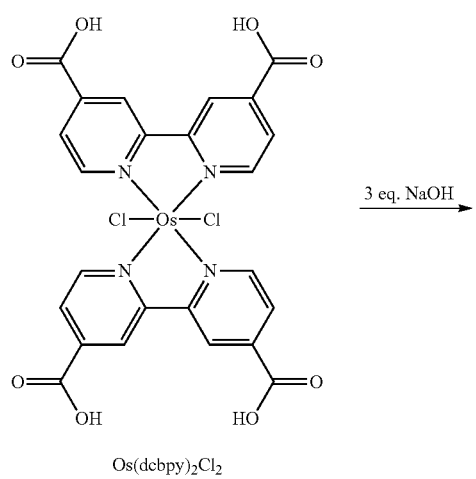

Os(dcbpy)₂Cl₂

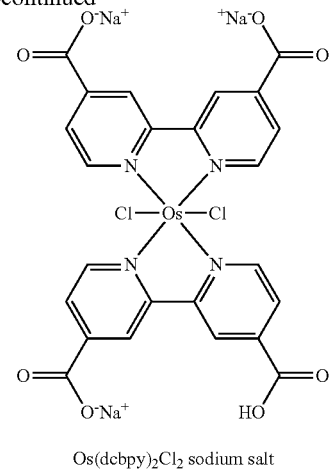

Os(dcbpy)₂Cl₂ sodium salt

An example of the present invention relates to an electron transfer mediator comprising an osmium complex which reacts with GDH, has no effect of oxygen partial pressure and stably maintains a redox state for a long time. The osmium complex is represented by Chemical Formula 1 as described above.

An embodiment of the electrochemical biosensor may include an enzyme capable of oxidizing and reducing an analyte in a liquid biological sample, and an electron transfer mediator. The electron transfer mediator may include an osmium complex or a salt thereof as a single component, or as a main component. Further, the electron transfer mediator may comprise an osmium complex or its salt as a main component, and in some embodiments does not contain a metal complex other than an osmium complex or its salt.

A further embodiment relates to a reagent for redox reaction, preferably an electrochemical biosensor, comprising an electron transfer mediator comprising an osmium complex and an oxidoreductase.

In another aspect, there is provided a method of preparing a reagent for a redox reaction with improved stability, comprising mixing an oxidoreductase and an electron transfer mediator. In an embodiment, the reagent composition for redox reaction may be applied to an electrochemical biosensor, and thus, in another example, a method of preparing a reagent for electrochemical biosensor with improved stability, comprising a step of mixing an oxidoreductase and an electron transfer mediator.

Another embodiment provides an electrochemical biosensor comprising the reagent composition for an electrochemical biosensor with improved stability.

In an electron transfer mediator, a reagent composition for redox reaction, and a electrochemical biosensor according to the present invention, the electron transfer mediator is reduced by performing the redox reaction with the reduced enzyme which is produced by the metabolite, and then can produce the current on the surface of electrode applied by the oxidative potential. In an electron transfer mediator, a reagent composition for redox reaction, and an electrochemical biosensor according to the present invention, the osmium complex or its salts can be used as a single component, or in combination with at least one of second electron transfer mediator.

In an electron transfer mediator, a reagent composition for redox reaction, and an electrochemical biosensor according to the present invention, the osmium complex may be used as an osmium complex itself, or a salt of an osmium complex, an oxidized compound of an osmium complex, or oxidized compound of its salt.

According to an embodiment of the present invention, in the reagent composition for redox reaction and the electrochemical biosensor, (a) an oxidoreductase and (b) an osmium complex, a salt compound of an osmium complex, an oxidized compound of an osmium complex, or a compound obtained by oxidizing a salt compound of the osmium complex, and (c) an oxidizing agent. When the oxidizing agent (c) is further contained, the component (b) is an osmium complex or a salt compound thereof which is not oxidized. The oxidizing agent may be at least one selected from the group consisting of NaOCl, $H_2O_2$, $O_2$, $O_3$, $PbO_2$, $MnO_2$, $KMnO_4$, $ClO_2$, $F_2$, $Cl_2$, $H_2CrO_4$, $K_2Cr_2O_7$, $N_2O$, $Ag_2O$, $OsO_4$, $H_2S_2O_8$, pyridinium chlorochromate and 2,2'-Dipyridyldisulfide.

The amount of the oxidizing agent added to the reagent composition for redox reaction according to the present invention is not particularly limited as long as it provides the oxidation state of the osmium complex. For example, the amount of the oxidizing agent may be 0.1 to 10 molar ratios on the basis of 1 mole of the osmium complex.

According to an embodiment of the present disclosure, the use of an osmium complex in combination of the second electron transfer mediator can significantly increase the glucose detection performance and minimize the effect of various interfering substances for glucose detection.

A reagent composition according to the present invention may contain 20 to 700 parts by weight, for example, 60 to 700 parts by weight or 30 to 340 parts by weight of the osmium complex based on 100 parts by weight of the redox enzyme. The content of the osmium complex can be appropriately adjusted according to the activity of the oxidoreductase. If the activity of the oxidoreductase contained in the reagent composition is high, the reagent composition can exhibit the desired effect, even if the content of the metal complex is low. Thus, as the activity of the oxidoreductase is higher, the content of the metal-containing complex may be adjusted to the relatively low content.

Unlike the conventional ruthenium complex, the osmium complex alone is used in the reagent compositions of the present invention; it can function as an electron transfer mediator sufficiently. The present invention can additionally include a second electron transfer mediator other than the metal complex.

The second electron transfer mediator is selected from the group consisting of 1-Methoxy-5-methylphenazinium methyl sulfate (1-methoxyPMS), 3-amino-7-(2,3,4,5,6-pentahydroxy hexanamido)-5-phenothiazinium, 1-Methoxy-5-methylphenazinium, Azure C, Azure A, Methylene Blue, Toluidine Blue and derivatives thereof.

When the electron transfer mediator is a mixture of an osmium complex and thionine or a derivative thereof, and/or a mixture of an osmium complex with 1-methoxy PMS or a derivative thereof, the molar ratio of thionine or 1-methoxy PMS to osmium complex (mole of thionine or 1-methoxy PMS: mole of osmium complex) can be from 1:1 to 20, specifically from 1:1 to 10.

The oxidoreductase refers to an enzyme that catalyzes the oxidation-reduction reaction of a living body. In the present invention, the oxidoreductase means an enzyme that is reduced by reacting with the target substance to be measured, such as the metabolite to be measured in the biosensor. The reduced enzyme may react with the electron transfer mediator and generate signal such as current change and the metabolite is quantified by measuring the signal such as the current change occurring at this time. The oxidoreductase used in the present invention may be at least one selected from the group consisting of various dehydrogenases, oxidases, esterases, and the like. Depending on the redox reaction or target substance, an enzyme adopting the substrate as a target substance can be selected and used among the enzymes belonging to the enzyme group.

In some embodiments, the oxidoreductase can be at least one selected from the group consisting of glucose dehydrogenase, glutamate dehydrogenase, glucose oxidase, cholesterol oxidase, cholesterol esterase, lactate oxidase, ascorbic acid oxidase, alcohol oxidase, alcohol dehydrogenase and bilirubin oxidase.

Meanwhile, the oxidoreductase may include a cofactor for storing hydrogen taken from a target substance (for example, a metabolite) to be measured. For example, the cofactors may be at least one selected from the group consisting of flavin adenine dinucleotide (FAD), nicotinamide adenine dinucleotide (NAD), and pyrroloquinoline quinone (PQQ).

Meanwhile, the oxidoreductase may be contained in combination with a cofactor for storing hydrogen taken from a target substance (for example, a metabolite) to be measured. For examples, when measuring the blood glucose concentration by using glucose dehydrogenase (GDH) as an oxidoreductase, the combination of cofactors and the oxidoreductase may include flavin adenine dinucleotide-glucose dehydrogenase (FAD-GDH) and/or nicotinamide adenine dinucleotide-glucose dehydrogenase containing FAD.

In an embodiment, the available oxidoreductase may be at least one selected from the group consisting of FAD-GDH (e.g. EC 1.1.99.10 etc.), NAD-GDH (e.g. EC 1.1.1.47 etc.), PQQ-GDH (e.g. EC1.1.5.2 etc.), Cholesterol oxidase (for example, EC 1.1.3.6 and the like), cholesterol esterase (for example, EC 3.1.3.2 and the like), glutamate dehydrogenase (for example, EC 1.4.1.2 and the like), glucose oxidase 1.13), lactate oxidase (for example, EC 1.1.3.2 etc.), ascorbic acid oxidase (for example EC 1.10.3.3 etc.), alcohol oxidase (for example EC 1.1.3.13 etc.), alcohol dehydrogenase, EC 1.1.1.1 etc.), bilirubin oxidase (EC 1.3.3.5 etc.), and the like.

Meanwhile, in other embodiments the reagent composition according to the present invention may contain at least one additive selected from the group consisting of a surfactant, a water-soluble polymer, a quaternary ammonium salt, a fatty acid, a thickening agent, etc. as a dispersant for dissolving a reagent, or a, adhesive agent for preparing a reagent, a stabilizer for long-term storage, and the like.

The surfactant may make the reagent spread evenly over the electrode, so as to dispense the reagent at a uniform thickness, when the reagent is dispensed. The surfactant may be at least one selected from the group consisting of Triton X-100, sodium dodecyl sulfate, perfluorooctane sulfonate, sodium stearate, and the like. The reagent composition of present invention may contain the surfactant at an amount of 3 to 25 parts by weight, for example 10 to 25 parts by weight based on 100 parts by weight of oxidoreductase, in order that the surfactant makes the reagent spread evenly over the electrode and be dispensed at a uniform thickness. For example, when the used oxidoreductase has an activity of 700 U/mg, the amount of surfactant may be used at 10 to 25 parts by weight based on 100 parts by weight of oxidoreductase. If the activity of the oxidoreductase is higher than the activity, the content of the metal-containing complex can be adjusted to the relatively low content.

The water-soluble polymer may serve as a polymer support in the reagent composition to help stabilize and disperse the enzyme. Examples of the water-soluble polymer include at least one selected from the group consisting of polyvinyl pyrrolidone (PVP), polyvinyl alcohol (PVA), perfluorosulfonate, hydroxyethyl cellulose (HEC), hydroxypropyl cellulose (HPC), carboxymethyl cellulose (CMC), cellulose acetate, polyamide, and the like. The reagent composition may contain 10 to 70 parts by weight, for example 30 to 70 parts by weight of the water-soluble polymer, based on 100 parts by weight of the oxidoreductase, in order to help stabilize and disperse the enzyme sufficiently. For example, when an oxidoreductase having an activity of 700 U/mg is used, it may contain 30 to 70 parts by weight of the water-soluble polymer based on 100 parts by weight of the oxidoreductase. When the activity of the oxidoreductase is higher than the activity, the content of water-soluble polymer can be adjusted lower than the range.

The water-soluble polymer may have a weight average molecular weight of about 2,500 to 3,000,000, for example, about 5,000 to 1,000,000 in order to effectively help stabilization and dispersion of the polymer support and the enzyme.

The quaternary ammonium salt may serve to reduce the measurement error which depends on the amount of hematocrit. The quaternary ammonium salt may be at least one selected from the group consisting of ecyltrimethyl ammonium, myristyltrimethyl ammonium, cetyltrimethyl ammonium, octadecyltrimethyl ammonium, tetrahexyl ammonium, and the like. A reagent composition according to the present invention may contain the quaternary ammonium salt at an amount of 20 to 130 parts by weight, for example 70 to 130 parts by weight, based on 100 parts by weight of the oxidoreductase enzyme, in order to efficiently reduce the measurement error according to the hematocrit. For example, when an oxidoreductase having an activity of 700 U/mg is used, it may contain 70 to 130 parts by weight of a quaternary ammonium salt based on 100 parts by weight of the oxidoreductase. When the activity of the oxidoreductase is higher than that, the content of quaternary ammonium salt can be adjusted to a lower level.

In some embodiments, the fatty acid serves to reduce the measurement error according to the amount of hematocrit, as the quaternary ammonium salt described above and to expand the linear dynamic range of the biosensor in the high concentration region. The fatty acid may be at least one selected from the group consisting of a fatty acid having a C4 to C20 carbon chain and a fatty acid salt thereof, preferably a fatty acid having an alkyl carbon chain of C6 to C12 or a fatty acid salt thereof. Examples of the fatty acid include at least one selected from the group consisting of caproic acid, heptanoic acid, caprylic acid, octanoic acid, nonanoic acid, capric acid, undecanoic acid, lauric acid, tridecanoic acid, myristic acid, pentadecanoic acid, palmitic acid, heptadecanoic acid heptadecanoic acid, stearic acid, nonadecanoic acid, arachidonic acid, salts of fatty acids, and the like. The reagent composition according to the present invention may contain 10 to 70 parts by weight, for example 30 to 70 pars by weight of the fatty acid with respect to 100 parts by weight of the oxidoreductase, in order to appropriately obtain the reduced measurement error depending on the hematocrit and the expansion effect of a linear dynamic range of the biosensor in a high concentration region. For example, when an oxidoreductase having an activity of 700 U/mg is used, it may contain 30 to 70 parts by weight of fatty acid based on 100 parts by weight of the oxidoreductase. When the activity of the oxidoreductase is higher than that, the content of fatty acid can be adjusted to lower level.

In some embodiments, the thickening agent serves to firmly attach the reagent to the electrode. The thickening agent may be one or more selected from the group consisting of Natrozol, diethylaminoethyl-Dextran hydrochloride (DEAE-Dextran hydrochloride), and the like. The reagent composition according to the present invention may contain the thickening agent in an amount of 10 to 90 parts by weight, for example 30 to 90 parts by weight, based on 100 parts by weight of the oxidoreductase, so that the reagent is firmly attached to the electrode. For example, when an oxidoreductase having an activity of 700 U/mg is used, it may contain 30 to 90 parts by weight of the oxidoreductase, based on 100 parts by weight of the oxidoreductase. When the activity of the oxidoreductase is higher than that, the amount can be adjusted lower than this.

In addition, embodiments of the present invention provide an electrochemical biosensor containing the reagent composition. In one embodiment, the electrochemical biosensor can be prepared by coating an osmium complex or its salt compound having the Chemical formula (1) and an enzyme capable of oxidizing and reducing an analyte in a liquid biological sample on a substrate having at least two electrodes and drying it. For example, an electrochemical biosensor is provided with a working electrode and an auxiliary electrode formed on one plane, where the reagent composition according to the present invention is contained on the working electrode.

According to another embodiment, in the electrochemical biosensor, the working electrode and the auxiliary electrode are provided so as to face each other on different planes, and the reagent composition according to the present invention is contained on the working electrode.

The form of the reagent composition according to the present invention applied to the biosensor is not particularly limited, but may be specifically coated on the surface of the working electrode, but is not limited thereto.

The planar-type and face-to-face type electrochemical biosensors according to the present invention can be manufactured according to the method disclosed in the prior art, for example, as described in KR10-2004-0105429A, KR10-2006-0089464A, KR10-0854389B, KR10-2008-0080841 A, KR10-2008-0084030A, KR10-2008-0088028A and the like.

Hereinafter, the structures of the planar and face-type electrochemical biosensors will be described with reference to FIG. 1 and FIG. 2.

The planar-type electrochemical biosensor in FIG. 1 includes a working electrode and an auxiliary electrode located on the same plane. From the top to the bottom direction, upper plate 11 equipped with air-discharging air outlet 10 for making the blood spread into the sensor; middle plate 9 adhering the upper plate and the lower plate by using the adhesive layers on both sides and making blood spread into the electrode due to the blood capillarity; a reagent composition 8 of present invention contained in the working electrode and auxiliary electrode (counter electrode), for example by coating; an insulating plate 7 equipped the channel part for defining the areas of working electrode and auxiliary electrode; the working electrode 2 and the auxiliary electrode on the lower plate 3; and a lower plate 1 where the working electrode and the auxiliary electrode are formed, are sequentially stacked structure.

The face-to-face type electrochemical biosensor in FIG. 2 includes a working electrode and an auxiliary electrode on the different plane. From the top to the bottom direction, a upper plate 11 equipped with air outlet 10 for making the blood spread into the sensor and an auxiliary electrode printed thereon; an auxiliary electrode 3 printed on the upper plate; middle plate 9 adhering the upper plate and the lower plate by using the adhesive layers on both sides and making blood spread into the electrode due to the blood capillarity; a reagent composition 8 of present invention contained in the working; an insulating plate 7 equipped the channel part for defining the areas of working electrode and auxiliary electrode; working electrode 2 printed on the lower plate; a lead 4 of auxiliary electrode; flow-sensing electrode 6 for detecting the blood input rate; and a lower plant 1 where the working electrode, the lead of auxiliary electrode and the flow-sensing electrode are sequentially stacked structure.

The electron transfer mediator of the present invention has advantages of reacting with GDH, no effect of oxygen partial pressure, stable maintenance of reduced and oxidized state for a long time, and thus an reagent for redox reaction and an electrochemical biosensor including the electron transfer mediator can minimize the measurement error caused by the oxygen partial pressure and be used stably for a long time.

EXAMPLES

Hereinafter, the present invention will be described referring to the following examples. However, these examples are merely illustrative of the present invention, the scope of which shall not be limited thereto. Examples of compositions and methods of making the same are herein disclosed.

Example 1: Preparation of Osmium Complex 1-1. Synthesis of Osmium Complex 4,4'-Dicarboxy-2,2'-Bipyridine (Dcbpy) and $K_2OsCl_6$ were Used as Starting Materials to Synthesize $Os(Dcbpy)_2Cl_2$ (Osmium Complex).

$K_2OsCl_6$ 0.481 g (1 mM) and dcbpy 0.488 g (2 mM) were poured into a 500 mL three-neck round-bottom flask, and dissolved with agitation for 1 hour by addition of dimethylformamide (DMF) 40 mL. Then, the mixture was incubated in an oil bath at 180° C. for 2 hours in an atmosphere of $N_2$ with reflux. After the solution was completely reacted, the solvent was removed using a rotary evaporator, the product was filtered under reduced pressure while washing with distilled water. The filtered product was dried at 50° C. for 12 hours, to produce $Os(dcbpy)_2Cl_2$ (osmium complex) at a yield of 60/%.

1-2. Spectroscopic Characterization:

To test the successful synthesis of $Os(dcbpy)_2Cl_2$ (osmium complex) by using dcbpy and $K_2OsCl_6$, 1H NMR (400 MHz, DMSO-d6) of the product was measured. 1H NMR spectrum of dcbpy (a) and osmium complex (b) is shown in FIG. 3.

As shown in FIG. 3, as the dcbpy ligand is coordinated to the central metal Os, the band width of H peak of —COOH substituted in the aromatic ring (FIG. 3 (b) 1) was still wider than that measured before the coordination to the central metal Os (FIG. 3 (a) 1). It is generally known that when the organic compound is coordinated to the metal, the band width of the peak tends to widen. The 1H NMR spectrum of the reaction shows that the reaction has proceeded successfully.

1-3. Electrochemical Characterization:

To verify the electrochemical properties of osmium complex, cyclic voltammetry was performed. Using a carbon electrode as the working electrode, platinum as the auxiliary electrode, and an Ag/AgCl (sat. KCl) electrode as a reference electrode, the current was measured by changing the glucose concentration in a mixed solution including FAD-glucose dehydrogenase (FAD-GDH) 10 mg/mL, osmium complex 30 mmol and 0.1 M PBS (pH 7.4). The current was measured in the ranges of −0.2 V~0.3 V at scan rate 10 mV/sec., the measurement result being shown in FIG. 4.

As shown in FIG. 4, the response slope of 77.1 nA/(mg/dL) and relatively excellent linearity were shown in the ranges of 90 mg/dL to 540 mg/dL of glucose concentration. The spectroscopic result of FIG. 3 and the electrochemical result of FIG. 4 confirmed that the osmium complex was synthesized successfully.

Example 2: Preparation of a Salt of Osmium Complex

The structure of the synthesized osmium complex is an organometallic compound where a dcbpy ligand having a by pyridine structure with a carboxy group (COOH) is coordinated to osmium (Os) as a central metal, and has low solubility in water. The solubility was increased by converting the —COOH group of the osmium complex to the salt form by substituting with —COO—Na+. First, the equivalence ratio was determined by titration to convert to the salt form, and the proper equivalence ratio was 1:3. In subsequent examples, an osmium complex sodium salt was used by substituting the osmium complex with NaOH at 1:3 equivalent ratios.

Example 3: Oxidative Treatment of Osmium Complex

In this example, 0.75 g (1 mM) of the synthesized osmium complex was poured to 500 mL one-neck round-bottom flask and was dissolved in 100 mL of distilled water. After 0.037 g/0.034 g (1 mM) of oxidizing agent ($NaOCl/H_2O_2$) was added, the reaction was carried out for 2 hours with agitation. After the reaction was completed, the solvent was removed using a rotary evaporator, and the product was filtered under reduced pressure while washing with ethyl ether. The filtered product was dried at 50° C. for 12 hours or more to obtain 90% osmium complex (oxidation state, Os(ox) complex).

Example 4: Stability Test of Osmium Complex

In order to confirm the stability of the osmium complex as an organometallic compound, the UV-visible spectrum change over time in aqueous solution was compared with that of ruthenium hexamine and Ferricyanide, which were commercially used as electron transfer media in glucose strip sensors.

Specifically, the UV-visible spectrum of an aqueous solution of 1 mg of each osmium complex, ruthenium hexamine, and Ferricyanide dissolved in 1 mL of 0.1 M PBS (pH 7.4) was measured and stored at room temperature for 11 days. The experimental results are shown in FIGS. 5A to 5C.

As shown in FIG. 5b, no change in the UV-visible spectrum was observed over time in the case of ruthenium hexamine (FIG. 5b), indicating that the oxidized Ru (III) was very stable. In the case of the osmium complex (FIG. 5a) synthesized in Example 1, the absorbance of absorption peaks at 400 nm and 520 mm decreased with time. At the initial stage, the oxidation state Os (III) and the reduced state Os (II) were mixed and the reduced state Os (II) were changed into the oxidation state Os (III) with time. The result indicates that the oxidation state Os (III) is more stable than reduced state Os (II) in an aqueous solution at room temperature. In case of Ferricyanide, the absorption peaks of 300 nm and 420 mm decreased with time, and the absorbance at 260 nm absorption peak increased, indicating that the oxidized Fe (III) was changed into reduced state Fe (II). These results show that the reduced Fe (II) is more stable than the reduced Fe (III).

Example 5: Biosensor Manufacture 5-1. Manufacture of Biosensor:

An Os-based glucose strip sensor was manufactured by using carbon as a working electrode, Ag/AgCl face-to-face sensor, osmium complex 30 mM, FAD-GDH 10 mg/mL, surfactant, and 0.1 M PBS (pH 7.4) of background electrolyte. The electrochemical properties such as response activity, stability, effect of oxygen partial pressure of the strip sensor was measured and compared with those of three type glucose strip sensors using CareSens N (Ru+GOx), CareSens Pro (Fe+GDH) or VetMate (Ru+GDH+Thionin). The response activity was measured with multi-channel biosensor system at the applied voltage of 0.2V.

5-2. Property Changes Over Time in Storage Conditions:

The properties such as background current and response slope for an Os-based glucose strip sensor over time in storage conditions were analyzed. A 30 mM Os-based glucose strip sensor, and three glucose strip sensors using CareSens N, CareSens Pro and VetMate were stored at 23° C., RH 20% or lower, and tested for property changes over time in storage conditions.

Three glucose strip sensors using CareSens N, CareSens Pro and VetMate maintained the background current and response slope, but in case of the Os-based glucose strip sensor under the general storage conditions, the background current was changed from 3.2 μA to 2.5 μA over time (FIG. 6). The experimental result was in accord with that of UV-visible spectrum which was performed for osmium complex under room temperature in Example 4.

5-3. Comparison of Effect of Oxygen Partial Pressure:

In order to remove the difference in the measured values of capillary blood and venous blood caused by the different oxygen partial pressure ($pO_2$), GDH is used (instead of GOx enzymes which rely on Oxygen) which is not effected by oxygen partial pressure, and may be used as an effective electron transfer mediator.

The effect of oxygen partial pressure was tested for a 30 mM Os-based strip, and three strips using CareSens N, CareSens Pro and VetMate.

The oxygen partial pressure was obtained by measuring the glucose concentrations of low (90 mg/dL), middle (200 mg/dL) and high (400 mg/dL) at saturated state (160 mmHg) and low-pressure state (40 mmHg) applied by a deoxidation process. The % error caused by the oxygen partial pressure was calculated by using the following formula.

$$\% \text{ Error} = \frac{I_{40\ mmHg} - I_{160\ mmHg}}{I_{40\ mmHg}} \quad \text{Formula 1}$$

The Ru-based strip (CareSens N, VetMate) showed about 8% error, but the 30 mM Os-based strip showed about 3% or lower error (FIG. 7).

Example 6: Test of Strip Sensor Properties Using the Osmium Complex with the Addition of Oxidizing Agent or the Osmium Complex Treated with Oxidizing Agent 6-1. Test of Strip Sensor Properties Using the Osmium Complex with the Addition of Oxidizing Agent:

On the basis of the experiment described above, an Os-based strip sensor was manufactured by adding an oxidizing agent and tested for the background current and the change of the background current with the addition of oxidizing agent over time.

A. Addition of NaOCl

Os-based glucose strip sensors were manufactured by using carbon as a working electrode, Ag/AgCl face-to-face sensor, and two kinds of base compositions including 20 mM of osmium complex or 30 mM of osmium complex, FAD-GDH 10 mg/mL, surfactant, and 0.1 M PBS (pH 7.4) of background electrolyte, or two compositions including the base compositions and $H_2O_2$. The electrochemical properties such as response activity, stability, and effect of oxygen partial pressure of the strip sensor were measured and compared with those of three type glucose strip sensors using CareSens N and CareSens Pro2. The response activity was measured with a multi-channel biosensor system at the applied voltage of 0.2V.

Four kinds of Os-based strip sensors, CareSens N and CareSens Pro 2 were stored at 23° C., RH 20% or lower, and tested for property changes over time in storage conditions.

When being compared with the conventional strip sensor having no addition of NaOCl, an Os-based strip including the NaOCl showed the change in background current from about 2 μA to about 0.2 μA, and showed comparatively stable background current over time under storage conditions (FIG. 8).

B. Addition of $H_2O_2$

Os-based glucose strip sensors were manufactured by using carbon as a working electrode, Ag/AgCl face-to-face sensor, and two kinds of base composition including 20 mM of osmium complex or 30 mM of osmium complex, FAD-GDH 10 mg/mL, surfactant, and 0.1 M PBS (pH 7.4) of background electrolyte, two compositions including the base compositions and $H_2O_2$, one composition with two-fold amount of GDH and 30 mM of osmium complex.

For the five kinds of Os-based strip sensors, the electrochemical properties such as response activity, stability, effect of oxygen partial pressure of the strip sensor were measured and compared with those of two glucose strip sensors using CareSens N and CareSens Pro2.

The response activity was measured with a multi-channel biosensor system at the applied voltage of 0.2V.

Five kinds of Os-based strip sensors, CareSens N and CareSens Pro 2 were stored at 23° C., RH 20% or lower, and tested for property changes over time in storage conditions.

As shown in FIG. 9, the Os-strip sensor with the addition of $H_2O_2$ showed about 0.2 μA of background current and a response slope of 20 nA/(mg/dL) or higher, compared with that of Os-strip sensor with the addition of NaOCl.

6-2. Test of Strip Sensor Properties Using the Osmium Complex Treated with Oxidizing Agent:

A. Oxidative Treatment with $H_2O_2$

Os-based glucose strip sensors were manufactured by using carbon as a working electrode, Ag/AgCl face-to-face sensor, and two kinds of base compositions including 20 mM of osmium complex or 30 mM of osmium complex, FAD-GDH 10 mg/mL, surfactant, and 0.1 M PBS (pH 7.4) of background electrolyte, two compositions including the osmium complex treated with $H_2O_2$(Os(ox)) and two compositions including the salt of oxidized osmium complex (Os(ox) salt). For six kinds of Os-based strip sensors, the electrochemical properties such as response activity, stability, effect of oxygen partial pressure of the strip sensor were measured and compared with those of two glucose strip sensors using CareSens N and CareSens Pro2.

The response activity was measured with a multi-channel biosensor system at the applied voltage of 0.2V.

Six kinds of Os-based strip sensors including 6 kinds of compositions, CareSens N and CareSens Pro 2 were stored at 23° C., RH 20% or lower, and tested for property changes over time in storage conditions.

The Os(ox) complex-based strip sensor including the Os complex treated with $H_2O_2$ showed about 0.2 μA of background current, which was similar to that of an Os complex-based strip sensor with the addition of $H_2O_2$. The Os(ox) salt-based strip sensor showed higher background current than that of Os(ox) complex-based strip sensor. Four kinds of Os(ox) complex-based strip sensors including the Os complex that were treated with $H_2O_2$ or Os(ox) salt showed the increased response slope, compared to the Os complex-based strip sensor with addition of $H_2O_2$(FIG. 10).

B. Oxidative Treatment with NaOCl

Os-based glucose strip sensors were manufactured by using carbon as a working electrode, Ag/AgCl face-to-face sensor, and two kinds of base compositions including 20 mM of osmium complex or 30 mM of osmium complex, FAD-GDH 10 mg/mL, surfactant, and 0.1 M PBS (pH 7.4) of background electrolyte, two compositions including the osmium complex treated with NaOCl (Os(ox)) and two compositions including the salt of oxidized osmium complex (Os(ox) salt). For six kinds of Os-based strip sensors, the electrochemical properties such as response activity, stability, effect of oxygen partial pressure of the strip sensor was measured and compared with those of two glucose strip sensors using CareSens N and CareSens Pro2.

The response activity was measured with a multi-channel biosensor system at the applied voltage of 0.2V.

Six kinds of Os-based strip sensors including 6 kinds of compositions, CareSens N and CareSens Pro 2 were stored at 23° C., RH 20% or lower, and tested for property changes over time in storage conditions.

The Os(ox) complex-based strip sensor including the Os complex treated with NaOCl showed excellent electrochemical response properties, such as low background current, response slope, stability with time, and decreased effect of oxygen partial pressure, among the Os-based strip sensors which were previously (FIG. 11 and FIG. 12).

To investigate the response properties of an Os(ox) complex strip sensor according to the applied voltage, Os-based glucose strip sensors were manufactured by using carbon as a working electrode, Ag/AgCl face-to-face sensor, and two kinds of base compositions including 20 mM of osmium complex or 30 mM of osmium complex, FAD-GDH 10 mg/mL, surfactant, and 0.1 M PBS (pH 7.4) of background electrolyte. The electrochemical properties were analyzed according to the applied voltage.

The response properties were measured at applied voltage of 0.1 V~0.4 V, at 0.05 V of interval, by using multi-channel biosensor system in which the applied voltage was easily changed.

FIG. 13 showed the changes in background current and response slope depending on the applied voltage. The background current showed a gradual increase from 0.2 V to 0.35 V and a sharp increase after 0.35 V, and the response slope increased rapidly to 0.3 V and then gradually increased after 0.3 V. When the applied voltage increased by 0.1 V to 0.3 V, the background current increased by 0.05 μA, while the response slope improved about two times, that is, by about 45 nA/(mg/dL).

Example 7: Long-Term Stability of a Strip Sensor Using the Osmium Complex Treated with NaOCl The strip sensor using the osmium complex treated with NaOCl was tested for the background current, response slope and effect of oxygen partial pressure over time under the storage conditions.

The response activity was measured with a multi-channel biosensor system at the applied voltage of 0.3V.

As shown in FIG. 14, the strip sensor including an Os (ox) complex oxidized with NaOCl maintained a stable background current and response slope for more than 8 weeks under storage conditions. As a result of calculating the % error using the current values of 70 mg/dL glucose and 100 mg/dL glucose over time, followed by calibrating in 20 to 200 mM range with the measurement result for 1 day, as shown in FIG. 15, the overall result was significantly valid by % error of 10% or less.

It was also found that the effect of oxygen partial pressure was also 4% or less (FIG. 16).

The strip sensor including FAD-GDH enzyme and Os (ox) complex oxidized with NaOCl stably maintained the effect of the background current, the response slope and the change in effect of oxygen partial pressure for 8 weeks under the storage conditions at room temperature.

The invention claimed is:

1. An electrochemical biosensor, comprising
   an electrode substrate, and
   an osmium complex represented by Chemical formula 1, Os(A)$m$X$n$, and an oxidizing agent,
   wherein, A is represented by Chemical formula 2,

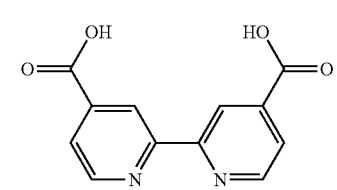

Chemical formula 2 wherein X is a halogen, m is an integer of 1 to 3, n is an integer of 0 to 4, and a sum of m and n is an integer of 3 to 5, or a salt thereof;
   an enzyme being capable of oxidizing and reducing a target substance in a liquid biological sample, wherein said complex and said enzyme are immobilized on the electrode substrate; and
   at least one selected from the group consisting of surfactants, water-soluble polymers, quaternary ammonium salts, fatty acids, and thickening agents,
   wherein the oxidizing agent is in a molar ratio of 0.1 to 10, based on 1 mole of osmium complex or its salt.

2. The electrochemical biosensor according to claim 1, wherein the electrochemical biosensor comprises a salt of the osmium complex of Chemical formula 1, and the salt is a salt of at least one alkali metal selected from the group consisting of Li salt, Na salt, K salt, Rb salt, Cs salt and Fr salt.

3. The electrochemical biosensor according to claim 1, wherein the osmium complex comprises trivalent osmium (III).

4. The electrochemical biosensor according to claim 1, wherein the osmium complex comprises trivalent osmium (III) and divalent osmium (II).

5. The electrochemical biosensor according to claim 1, wherein the osmium complex is obtained by using the compound represented by Chemical formula 2, and the compound represented by Chemical formula 6:

$Y_p OsX_q$, wherein, Y is K, Na or $NH_4$, X is a halogen, p is an integer of 1 to 2, and q is an integer of 1 to 6.

6. The electrochemical biosensor according to claim 1, wherein the oxidizing agent is at least one selected from the group consisting of NaOCl, $H_2O_2$, $O_2$, $O_3$, $PbO_2$, $MnO_2$, $KMnO_4$, $ClO_2$, $F_2$, $Cl_2$, $H_2CrO_4$, $K_2Cr_2O_7$, $N_2O$, $Ag_2O$, $OsO_4$, $H_2S_2O_8$, pyridinium chlorochromate and 2,2'-Dipyridyldisulfide.

7. The electrochemical biosensor according to claim 1 which does not comprises an organometallic compound other than the osmium complex or its salt as an electron transfer mediator.

8. The electrochemical biosensor according to claim 1, wherein the osmium complex or its salt is in the amount of 20 to 700 parts by weight based on 100 parts by weight of enzyme.

9. The electrochemical biosensor according to claim 1, wherein the biosensor further comprises a second electron transfer mediator, which is at least one selected from the group consisting of thionine, 1-Methoxy-5-methylphenazinium methylsulfate, 3-amino-7-(2,3,4,5,6-pentahydroxy hexanamido)-5-phenothiazinium, 1-Methoxy-5-methylphenazinium, Azure C, Azure A, Methylene Blue, Toluidine Blue, and derivatives thereof.

10. The electrochemical biosensor according to claim 9, wherein the enzyme is at least an oxidoreductase selected from the group consisting of dehydrogenase, oxidase and esterase; or at least an oxidoreductase selected from the group consisting of dehydrogenase, oxidase and esterase, in combination with at least a cofactor selected from the group consisting of flavin adenine dinucleotide (FAD), nicotinamide adenine dinucleotide (NAD), and Pyrroloquinoline quinone (PQQ).

11. The electrochemical biosensor according to claim 10, wherein the enzyme is at least one selected from the group consisting of flavin adenine dinucleotide-glucose dehydrogenase (FAD-GDH), and nicotinamide adenine dinucleotide-glucose dehydrogenase.

12. The electrochemical biosensor according to claim 10, wherein the at least an oxidoreductase selected from the group consisting of dehydrogenase, oxidase and esterase is at least one selected from the group consisting of glucose dehydrogenase, glutamate dehydrogenase, glucose oxidase, cholesterol oxidase, cholesterol esterase, lactate oxidase, ascorbic acid oxidase, alcohol oxidase, alcohol dehydrogenase and bilirubin oxidase.

13. The electrochemical biosensor according to claim 1, wherein the electrochemical biosensor comprises a surfactant and the surfactant is at least one selected from the group consisting of 4-(1,1,3,3-Tetramethylbutyl)phenyl-polyethylene glycol, sodium dodecyl sulfate, perfluorooctane sulfonate and sodium stearate.

14. The electrochemical biosensor according to claim 1, wherein the liquid biological sample is blood.

15. The electrochemical biosensor according to claim 1, wherein the electrochemical biosensor comprises water-soluble polymer and the water-soluble polymer is at least one selected from the group consisting of polyvinyl pyrrolidone (PVP), polyvinyl alcohol (PVA), perfluorosulfonate, hydroxyethyl cellulose (HEC), hydroxypropyl cellulose (HPC), carboxymethyl cellulose (CMC), cellulose acetate and polyamide.

16. The electrochemical biosensor according to claim 1, wherein the electrochemical biosensor comprises water-soluble polymer and the quaternary ammonium salt is at least one selected from the group consisting of ecyltrimethylammonium, myristyltrimethylammonium, cetyltrimethylammonium, octadecyltrimethylammonium and tetrahexylammonium.

17. The electrochemical biosensor according to claim 1, further comprising a fatty acid which is at least one selected from the group consisting of a fatty acid having a C4 to C20 carbon chain and a fatty acid salt thereof.

18. The electrochemical biosensor according to claim 1, further comprising a thickening agent which is one or more selected from the group consisting of hydroxyethylcellulose and diethylaminoethyl-Dextran hydrochloride (DEAE-Dextran hydrochloride).

* * * * *